US007390800B2

(12) United States Patent
Lee et al.

(10) Patent No.: US 7,390,800 B2
(45) Date of Patent: Jun. 24, 2008

(54) **ADENOSINE DEAMINASE INHIBITOR AND NOVEL *BACILLUS* SP. IADA-7 STRAIN WHICH PRODUCES IT**

(75) Inventors: Gwang Lee, Suwon-si (KR); Young Hwan Ahn, Seongnam-si (KR); Ki Ho Park, Busan (KR); Hong Ki Jun, Busan (KR)

(73) Assignee: FCB-Pharmicell Co., Ltd., Gyeonggi-do (KR)

( * ) Notice: Subject to any disclaimer, the term of this patent is extended or adjusted under 35 U.S.C. 154(b) by 261 days.

(21) Appl. No.: 10/550,301

(22) PCT Filed: Mar. 24, 2004

(86) PCT No.: PCT/KR2004/000652

§ 371 (c)(1),
(2), (4) Date: Sep. 22, 2005

(87) PCT Pub. No.: WO2004/085410

PCT Pub. Date: Oct. 7, 2004

(65) Prior Publication Data

US 2006/0211681 A1    Sep. 21, 2006

(30) Foreign Application Priority Data

Mar. 27, 2003    (KR) .................. 1020030019238

(51) Int. Cl.
*C07D 243/04*    (2006.01)
*A61K 31/551*    (2006.01)

(52) U.S. Cl. ........................ 514/218; 540/492
(58) Field of Classification Search ............. 540/492; 514/218
See application file for complete search history.

(56) References Cited

U.S. PATENT DOCUMENTS

| 4,935,505 A | 6/1990 | Townsend et al. ............ 536/24 |
| 5,705,491 A | 1/1998 | Yamada ...................... 514/46 |

FOREIGN PATENT DOCUMENTS

| EP | 156524 A2 | 10/1985 |
| WO | WO 00/55155 A2 | 9/2000 |
| WO | WO 00/56734 A1 | 9/2000 |

OTHER PUBLICATIONS

Agarwal, et al.; Tight-Binding Inhibitors—IV. Inhibition of Adenosine Deaminases by Various Inhibitors; Biochem Pharmacol. Mar. 1, 1977; 26(5): 359-67.
Aldrich, et al.; "The importance of Adenosine Deaminase for Lymphocyte Development and Function"; Biochem Biophys Res Commun. Jun. 7, 2000; 272(2):311-5.
Bielat, et al.; "ECTO-enzyme activity of human erythrocyte adenosine deaminase"; Mol Cell Biochem. Apr. 11, 1989;86(2):135-42.

Borroto-Esoda, et al.; "In vitro Combination of Amdoxovir and the Inosine Monophosphate Dehydrogenase Inhibitors Mycophenolic Acid and Ribavirin Demonstrates Potent Activity against Wild-Type and Drug-Resistant Variants of Human Immunodeficiency Virus Type 1"; Antimicrob Agents Chemother. Nov. 2004; 48(11): 4387-94.
Ciruela, et al.; "Adenosine deaminase affects ligand-induced signaling by interacting with cell surface adenosine receptors"; FEBS Lett. Feb. 19, 1996; 380(3): 219-23.
Cristalli, et al.; "Adenosine Deaminase Functional Implication and Different Classes of Inhibitors"; Med Res Rev. Mar. 2001; 21(2): 105-28.
Daddona, Peter E.; "Human Adenosine Deaminase: Properties and Turnover in Cultured T and B Lymphoblasts"; J Biol Chem. Dec. 10, 1981; 256(23): 12496-501.
Daluge, et al.; "1592U89, a Novel Carbocyclic Nucleoside Analog with Potent, Selective Anti-Human Immunodeficiency Virus Activity"; Antimicrob Agents Chemother May 1997; 41(5): 1082-93.
Dolezelova, et al.; "The emerging role of adenosine deaminases in insect"; Insect Biochem Mol. boil. May 2005; 35(5):381-9.
Fernandez, et al.; "Adenosine Deaminase Isoenzymes and Neopterin in Liver Cirrhosis"; J Clin Gastroenterol. Mar. 2000; 30(2): 181-6.
Franco, et al.; Enzymatic and extra enzymatic role of ecto-adenosine deaminase in lymphocytes, Immunol Rev. Feb. 1998; 161: 27-42.
Giblett, et al.; "Adenosine-Deaminase deficiency in two patients with severly impaired cellular immunity", Lancet. Nov. 18, 1972; 2(7786): 1067-9.
Grant, et al.; "Dialdehydes derived from Adenine Nucleosides as Substrates and Inhibitors of Adenosine Aminohydrolase".
Guan, et al.; Spiro pentane Mimics of Nucleosides: Analogues of 2'-Deoxyandenosine and 2'-Deoxyguanosine. Synthesis of All Stereoisomer, Isomeric Assignment, and Biological Activity.
Hirschhorn, et al.; "Adenosine Deaminase Activity in Normal Tissues and Tissues from a child with severe Combined Immunodeficiency and Adenosine Deaminase Deficiency"; Clin Immunol Immunopathol. Mar. 1978; 993: 287-92.
Hirschhorn, Rochelle; "Overview of Biochemical Abnormalities and Molecular Genetics of Adenosine Deaminase Deficiency"; Pedia Res. Jan. 1993 ;33 (1 Suppl): S35-41.
Ho, et al.; "Enzyme Activities of Leukemic Cells and Biochemical Changes Induced by Deoxycoformycin In Vitro- Lack of correlation with cynical Response"; Leuk Res. 1989; 13(4): 269-78.
Kelly, et al.; "Primary structure of bovine adensine deaminase"; (Abstract) J Pharm Biomed Anal. Aug. 1996; 14(11):1513-9.
Kelly, et al.; "Primary structure of bovine adensine deaminase"; J Pharm Biomed Anal. Aug. 1996; 14(11):1513-9.
Kodama, et al.; "Antileukemic Activity and Mechanism of Action of Cordycepin against Terminal Deoxynucleotidyl Transferase-Positive (TdT+) Leukemic Cells"; Biochem Pharmacol. Feb. 1, 2000; 59(3) 273-81.

(Continued)

*Primary Examiner*—Bruck Kifle
(74) *Attorney, Agent, or Firm*—Frommer Lawrence & Haug LLP; Ronald R. Santucci

(57) ABSTRACT

The present invention relates to an adenosine deaminase inhibitor and a novel *Bacillus* sp. strain which produces it. Particularly, the present 5 invention relates to the adenosine deaminase inhibitor, and the novel *Bacillus* sp. IADA-7 producing the above adenosine deaminase inhibitor. The adenosine deaminase inhibitor of the present Invention shows superior antibacterial and anticancer activities to the previously reported adenosine deaminase inhibitors.

4 Claims, 21 Drawing Sheets

OTHER PUBLICATIONS

Lerner, et al.; "Inhibition of Adenosine Deaminase by Alcohols Derived from Adenine Nucleosides"; biochemistry. Jul. 18, 1972; 11(15):2772-7.

Mills, et al.; "Purine metabolism in adenosine deaminase deficiency"; Proc Natl Acd Aci U S A. Aug. 1976; 73(8): 2867(71).

Mitchell, et al.; "Inhibition of Adensine Deaminase Activity Results in Cytotoxicity to T Lymphoblasts In Vivo"; Blook. Sep. 1980; 56(3) 556-9.

Pragnacharvulu, et al.; Adenosine Deaminase Inhibitors: Synthesis and Biological Evaluations of Unsaturated., Aromatic, and Oxo Derivatives of (+) -erythro-9-(2'S-Hydroxy-3'R-nonyl) adenine [(+)] -EHNA]; Biochem Biophys Res Commun. Jun. 7, 2000; 272(2):311-5.

Sawynok, et al.; "Peripheral Antinociceptive effect of an adensine kinase inhibitor, with augmentation by an adenosine deaminase inhibitor, in the rat formalin test"; Pain. Jan. 1998; 74(1):75-81.

Shi, et al.; "Diverse Genetic Regulatory Motifs Required for Murine Adenosine Deaminase Gene Expression in the Placenta"; J Biol Chem. Jan. 24, 1997; 272(4):2334-41.

Tanaka, et al.; "Potentiation of Cytotoxicity and Antitumor Activity of Adenosine Analogs by the Adenosine Deaminase Inihibitor Adecypenol"; J Antibot (Tokyo). Nov. 1989; 42(11):1722-4.

Tritsch, George L.; "Validity of the Continuous Spectrophotometric Assay of Kalckar for Adenosine Deaminase Activity"; Anal Biochem. Feb. 15, 1983; 129(1): 207-9.

TuNac, et al.; "2' Chloropentostatin: Discovery, Fermentation and biological Activity"; J Antibiot (Tokyo). Oct. 1985; 38(10): 1344-9.

Vellard, Michael; "The enzyme as drug: application of enzymes as pharmaceuticals"; Curr Opin Biotechnol. Aug. 2003; 14(4): 444-50.

Fig. 5

| | Vol. (ml) | Total Activity (units * 10³) | Yield (%) |
|---|---|---|---|
| Culture Broth | | | |
| ↓ | | | |
| Collect Supernatant by Centrifugation | 8,820 | 45,000 | 100 |
| ↓ | | | |
| Activated Charcoal Extraction | 100 | 31,050 | 69 |
| Extract with 80% Methanol concentrated in Vacuum | | | |
| Methanol Fractionation | 50 | 27,900 | 62 |
| Removal of Precipitate & Methanol | | | |
| Dowex 1x1-100(Cl⁻) | 50 | 23,100 | 51 |
| Washed with distilled water | | | |
| Dowex 50W-X4(H⁺) | 30 | 7,100 | 15 |
| Eluted with 0.2N NaOH, Evaporated NH₄OH | | | |
| Biogel P₂ Gel Filtration | 10 | 2,250 | 5 |
| Eluted with milipore water | | | |
| Reverse Phase TLC | 2 | 1,507 | 3 |
| Develop with a developing solution ( NH₄OH: C₂H₅OH:H₂O=6:4:1) | | | |
| Normal Phase TLC | 2 | 1,020 | 2 |
| Develop with a developing solution ( CHCl₃ CH₃OH =7:3), Extract with Methanol | | | |
| HPLC | | | |

Supernatant    Purified sample

ADENOSINE DEAMINASE INHIBITOR AND NOVEL *BACILLUS* SP. IADA-7 STRAIN WHICH PRODUCES IT

This application is a 371 of PCT/KR2004/000652 filed on Mar. 24, 2004, published on Oct. 7, 2004 under publication number WO 2004/085410 A1 which claims priority benefits from South Korean Patent Application Number 10-2003-0019238 filed Mar. 27, 2003.

FIELD OF THE INVENTION

The present invention relates to an adenosine deaminase inhibitor and a novel *Bacillus* sp. strain producing the same. Particularly, the present invention relates to the adenosine deaminase inhibitor of Formula 1 and the novel *Bacillus* sp. IADA-7 (KCTC 10446BP) producing the above adenosine deaminase inhibitor:

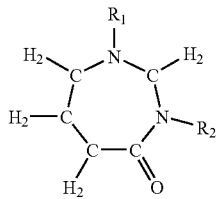

<Formula 1> wherein $R_1$ and $R_2$ are H or a $C_1$~$C_{10}$ alkyl group, respectively.

BACKGROUND OF THE INVENTION

Adenosine deaminase (adenosine aminohydrolase, EC 3.5.4.4), one of the enzymes involved in purine metabolism, generates inosine and ammonia by removing an amino group coupled to the sixth carbon of adenosine and is present ubiquitously in nature.

Purine is synthesized via two pathways: a de novo pathway from a micromolecule precursor and a salvage pathway from the purine.

The salvage pathway is a process which reuses a foreign substance such as a degrading product generated by destroying unstable RNA within a cell, a nucleic acid of dead cell and a degrading product of nucleotides, and has the advantage of preventing a loss in vital energy and precursors. While the de novo pathway is preserved in all species, the salvage pathway varies depending on the kind of species.

It has been known that animals, plants and microorganisms have a specific inhibitor for each enzyme reaction and these inhibitors are mostly macromolecule peptides, but an inhibitor for the adenosine deaminase is generally an adenosine analogue which is a micromolecule compound having 500 Da or less of a molecular weight. Further, it is known that an enzyme inhibitor isolated from a microbial metabolite is a micromolecular substance having an extremely low toxicity with a new structure. Some inhibitors are very similar in their structures. The pharmaceutical composition of the present invention substrates, while others are completely different from their substrates.

As shown in the biosynthesis of antibiotics, there are cases that a plasmid is involved in a characteristic part of the procedure for biosynthesizing an enzyme inhibitor.

There have been reports on several microorganism-originated inhibitors for adenosine deaminase, such as coformycin (3-(α-D-ribo-furanosyl)-6,7,8-trihydroimidazol(1,3)diazepin-8(R)-ol) produced by *Streptomyces kaniharaensis* SF-557; and cordycepsin and 2'-deoxy coformycin produced by *Aspergillus nidulans* Y-176-2.

Coformycin produced by *Streptomyces* which produces formycin(7-amino-3-(β-ribofuranosyl)pyrazolo(4,3-d)pyrimidine) is a specific inhibitor for the adenosine deaminase and its inhibition is in competition with a substrate. Further, coformycin, together with formycin, shows a synergistic effect in inhibiting a bacterial growth in most bacteria except for *Xanthomonas oryzae*, and effectively inhibits a proliferation of Yoshida rat sarcoma cells.

Further, it has been reported 9-α-D-mannopyranosyladenine(1), 9-β-D-xylopyranosyladenine(2), 9-α-D-arabinopyranosyladenine(3), 9-α-L-rhamnopyranosyladenine (4), 9-β-D-fucopyranosyl adenine(5), 9-β-L-fucopyranosyladenine(6) as adenosine deaminase inhibitors. All of them except for 9-α-D-mannopyranosyladenine(4) act as competitive inhibitors, and 9-α-L-rhamnopyranosyladenine is known to have the strongest inhibitory effect.

It has been known that cytotoxicity is developed in a cell inhibited by erythro-9-(2-hydroxy-3-nonyl)adenine), an inhibitor of an adenosine deaminase, when the cell is treated with adenosine and deoxyadenosine.

It has been also reported that injection of an adenosine analogue such as arabinosyladenine, codycepin or formycin as into an animal can increase an anti-cancer effect.

An enzyme inhibitor has been effectively used for analyzing human physiological functions and medically important pathological phenomena, and in particular, specific inhibitors have been known useful for biochemical analyses of biological functions or pathogens. Further, the enzyme inhibitors are powerful means in discovering various characteristics of enzymes such as active sites of enzymes, in vivo roles and physiological functions, and they can be also applicable as markers for diagnosing various diseases or as therapeutic agents.

The study on adenosine deaminase has been conducted since 1980s when an inhibitor of adenosine deaminase was known as an inhibitor of an immune system based on the discovery that the deficiency in adenosine deaminase, an essential factor involved in immune system, leads to the decrease in T-lymphocyte and B-lymphocyte thus resulting in an immunodeficiency.

Further, it has been found that the adenosine deaminase inhibitor increases the amount of ATP synthesis in petroleum-decomposing yeast using adenosine as a substrate, and thus its application to ATP synthesis has been proposed.

The studies about enzyme inhibitors have been actively carried out at numerous research institutions. As a result, new metabolic systems or enzyme systems have been discovered, thus clarifying the controlling relationships among biophysical functions.

Most of adenosine deaminase inhibitors reported till now have been grouped to a purine analogue family, which is produced by *Actinomycetes*, but they are very toxic to human cells when applied for medical treatments, and therefore, it has been on urgent need to develop a new drug applicable for clinical trials.

Further, there has been no report on adenosine deaminase inhibitors produced by bacterial strains.

The present inventors have isolated a new bacterial strain from a soil which produces an adenosine deaminase inhibitor compound and found that the inhibitor compound has antibacterial and anticancer activities.

SUMMARY OF THE INVENTION

Accordingly, an object of the present invention is to provide an adenosine deaminase inhibitor compound and a pharmaceutically acceptable salt thereof.

Another object of the present invention is to provide a novel *Bacillus* sp. IADA-7 (KCTC 10446BP) strain which produces the adenosine deaminase inhibitor and a method for producing same.

BRIEF DESCRIPTION OF THE DRAWINGS

The above and other objects and features of the present invention will become apparent from the following description of the invention, when taken in conjunction with the accompanying drawings, wherein

FIG. 5 shows a flowchart of representing a purifying procedure of the inhibitor compound of the present invention.

DETAILED DESCRIPTION OF THE INVENTION

Figure 1:
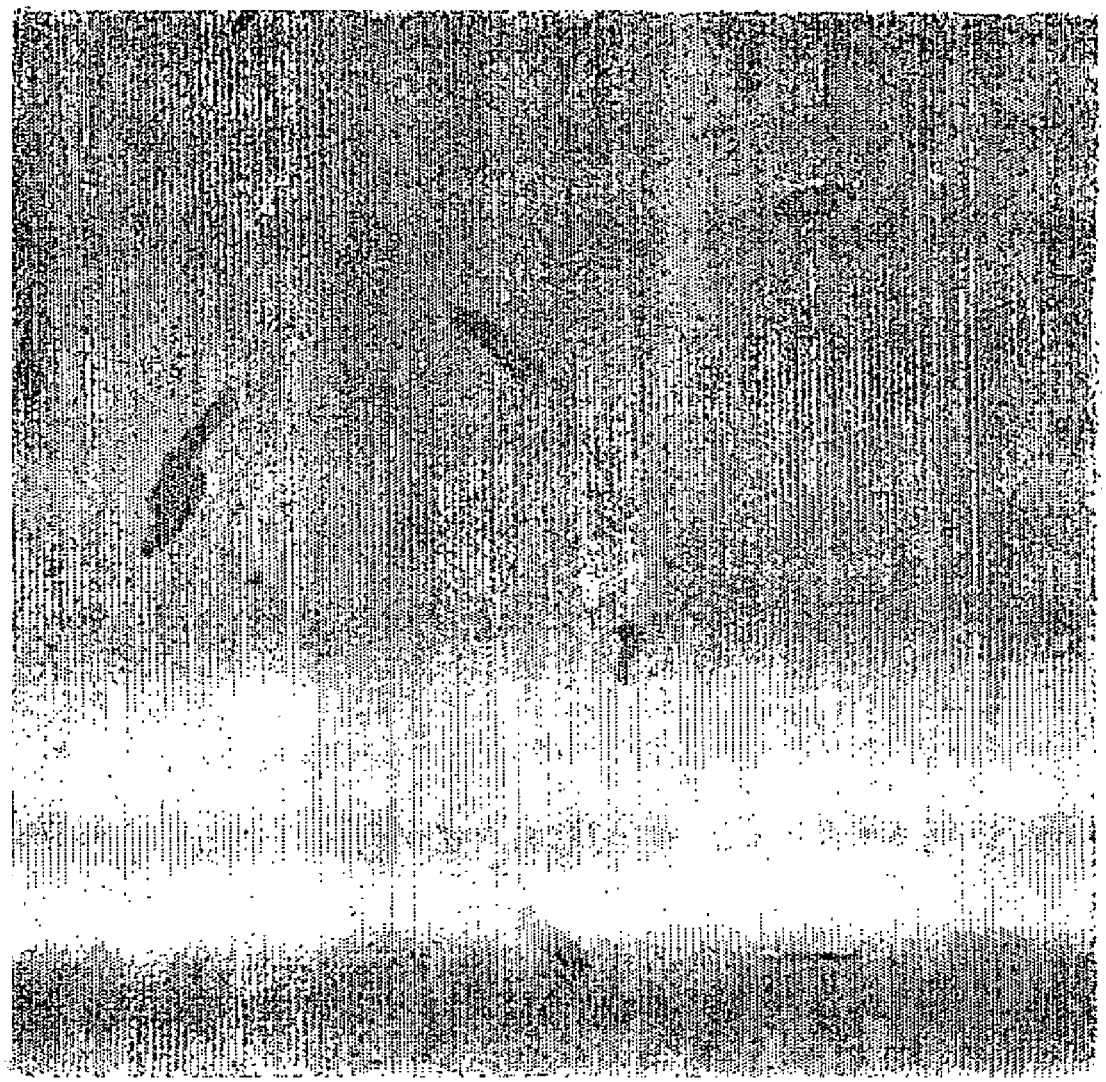
FIG. 1 shows an optical microphotograph of the *Bacillus* sp. IADA-7 (KCTC 10446BP) strain of the present invention.

In accordance with one aspect of the present invention, there is provided an adenosine deaminase inhibitor compound of Formula 1 and a pharmaceutically acceptable salt thereof:

<Formula 1> wherein $R_1$ and $R_2$ are H or a $C_1$–$C_{10}$ alkyl group, respectively.

The present invention also provides a pharmaceutical composition comprising the compound showing an adenosine deaminase inhibitory activity as an effective ingredient.

In addition, the present invention provides an antibacterial or an anticancer agent comprising a compound showing an adenosine deaminase inhibitory activity as an effective ingredient.

Further, the present invention provides a novel *Bacillus* sp. IADA-7 strain (KCTC 10446BP) which produces the compound of Formula 1.

Furthermore, the present invention provides a method for producing the compound of Formula 1 which comprises the steps of culturing the *Bacillus* sp. IADA-7 (KCTC 10446BP) strain and purifying the compound from the culture solution.

Hereinafter, the present invention is described in detail.

The present invention relates to the adenosine deaminase inhibitor of Formula 1 and the novel *Bacillus* sp. IADA-7 (KCTC 10446BP) producing the same.

The bacterial strain producing the adenosine deaminase inhibitor has been isolated from soil and its morphological, cultural and biochemical features have been characterized. As a result, the isolated bacterial strain has been identified as a *Bacillus* sp. and designated IADA-7. The *Bacillus* sp. IADA-7 strain of the present invention has been deposited at Korean Collection for Type Cultures (Address: #52, Oun-dong, Yusong-ku, Taejon 305-333, Republic of Korea) on Mar. 18, 2003 and assigned with the accession number of KCTC 10446BP, in accordance with the terms of the Budapest Treaty on the International Recognition of the Deposit of Microorganism for the Purpose of Patent Procedure.

Further, the present invention also includes a method for producing the compound of Formula 1 by culturing the *Bacillus* sp. IADA-7 (KCTC 10446BP) strain.

<Formula 1> wherein $R_1$ and $R_2$ are H or a $C_1$–$C_{10}$ alkyl group, respectively.

It has been confirmed that the compound of Formula 1 produced by the above-mentioned method shows high antibacterial and anticancer activities as an adenosine deaminase inhibitor.

Meanwhile, the compound of Formula 1 of the present invention may be used in a form of a pharmaceutically acceptable salt, and in particular, its acid added salt prepared by using a pharmaceutically acceptable free acid is preferable. A pharmaceutically acceptable acid added salt of the compound of Formula 1 may be prepared according to the conventional method well-known in the art. Inorganic and organic acids may be used as the free acid. The inorganic acid includes, but is not limited to, hydrochloric acid, bromic acid, sulfuric acid and phosphoric acid; and the organic acid, citric acid, acetic acid, lactic acid, tartaric acid, maleic acid, fumaric acid, formic acid, propionic acid, oxalic acid, trifluoroacetic acid, benzoic acid, gluconic acid, methansulfonic acid, glycolic acid, succinic acid, 4-toluenesulfonic acid, galacturonic acid, embonic acid, glutamic acid or asparaginic acid.

Accordingly, the pharmaceutical composition comprising the compound of Formula 1 or a pharmaceutically acceptable salt thereof as an effective ingredient can be effectively used for developing an antibacterial or an anticancer agent as an adenosine deaminase inhibitor.

The pharmaceutical composition of the present invention can be administered orally or via parental routes such as percutaneous, subcutaneous, intravenous or intramuscular methods, and manufactured in a form of a common medicine or a health improving food.

The pharmaceutical composition of the present invention may be formulated in the form of tablets, troches, soluble or oily suspensions, powders or granules, emulsions, hard or soft capsules, syrups or elixirs. Pharmaceutical formulations in the form of tablets and capsules may further comprise binding agents such as lactose, saccharose, sorbitol, manitol, starch, amylopectin, cellulose or gelatin; emulsifying agents such as dicalcium phosphate; disintegrating agents such as corn starch or sweet potato starch; and lubricating agents such as magnesium stearate, calcium stearate, sodium stearate, sodium stearylfumarate or polyglycol wax. In case of capsules, they may further comprise soluble carriers such as fat oil besides the above mentioned substances.

Further, the pharmaceutical composition may be parenterally administered via subcutaneous injection, intravenous injection, intramuscular injection or chest injection. Pharmaceutical formulations for parental administration may be prepared by mixing toluquinol in water with stabilizing agents or buffering agents to obtain a solution or a suspension and formulating the solution or the suspension into an ample or a vial as a unit dosage form.

For clinical administration purpose, a typical daily dose of the compound of Formula 1 may range from 1 to 50 mg/kg body weight, preferably from 5 to 20 mg/kg body weight and can be administered in a single dose or in divided dose. However, it can be changed into the higher or lower daily dose of the effective ingredient depending on a disease. Further, it should be understood that the amount of the effective ingredient actually administrated to a certain patient ought to be determined in light of various relevant factors including the kind of effective compound administered, body weight, age, sex, health conditions, diet and excretion rate of an individual patient, the selected route of administration, the combination of drugs and the seriousness of the patient's symptom.

Meanwhile, the culture and identification of a bacterial strain in the present invention have been carried out according to the methods as described below.

<Reagents and Equipments>

Bacteria were cultured in a 120Rev.×6 cm shaker and the removal of cultured bacterial cells and preparation of a crude enzyme solution were performed by using H50A-6 centrifuge (Han-il, Korea). Recording Spectrophotometer UV-240 (Shimadzu, Co. Ltd., Japan) was used to measure the growth and enzyme activity of the bacteria.

Activated charcoal, Dowex 1X1-100 (Cl—) and Dowex 50W-X4 ($H^+$) were purchased from Sigma Chemical Co. (St. Louis. 63178, USA); and Bio-gel $P_2$ gel for a gel filtration was purchased from Bio-Rad (USA). An animal derived adenosine deaminase was purchased from Sigma Chemical Co., which are 250 units of freeze-dried enzyme.

Silica gel G-60 and TLC-RP18$F_{254}$ (Merck) were used as a TLC plate for examining purities; Multiphore II (LKB 2117) for high voltage paper electrophoresis; and Model 510 (Waters, USA) for HPLC, wherein A PAK™ $C_{18}$ and UV detector 441 were used as column and a detector, respectively.

For structural analyses, FT-S-60 IR spectroscopy (Bio-Rad), NMR and GC-MASS (Hewlett-Packard) were used.

The following Examples and Test Examples are given for the purpose of illustration only, and they should not be construed as limiting the scope of the present invention.

EXAMPLE

Example 1

Isolation and Identification of *Bacillus* sp. IADA-7 (KCTC 10446BP) Strain

I. Isolation of a Bacterial Strain Producing Adenosine Deaminase Inhibitor

To isolate a bacterial strain producing an adenosine deaminase inhibitor, a soil sample collected from a certain area of Korea was air-dried at a dark place for 2 to 3 days. After about 0.5 g of the dried soil sample was suspended in 5 mL of distilled water and stood for a while, a supernatant taken from the suspension was spread onto the medium for isolating *Actinomycetes* (Medium A) having the following composition of Table 1 and cultured at 30° C.

TABLE 1

| Medium for isolating Actinomycetes (Medium A) | |
|---|---|
| Soluble starch | 1.0 g |
| $KH_2PO_4$ | 0.05 g |
| $NH_4Cl$ | 0.05 g |
| Agar | 1.7 g |
| Distilled water | 100 mL |
| Medium for synthesizing an inhibitor (Medium B) | |
| Glucose | 1.0 g |
| Yeast extract | 0.2 g |
| Meat extract | 0.2 g |
| Peptone | 0.2 g |
| $KH_2PO_4$ | 0.05 g |
| $MgCl_2.6H_2O$ | 0.01 g |
| Distilled water | 100 mL (pH 7.3) |
| Medium for storage (Medium C) | |
| Glucose | 1.0 g |
| Peptone | 0.2 g |
| Meat extract | 0.1 g |
| Yeast extract | 0.1 g |
| Agar | 1.8 g |
| Distilled water | 100 mL (pH 7.5) |
| Medium for main culture (Medium D) | |
| Glucose | 0.5 g |
| Peptone | 0.5 g |

TABLE 1-continued

| | |
|---|---|
| Yeast extract | 1.0 g |
| NH$_4$Cl | 0.5 g |
| Distilled Water | 100 mL (pH 7.0) |

Using the medium for isolating *Actinomycetes* as a medium for isolating a bacterial strain was intended to efficiently isolate a new bacterial strain by modifying an isolating condition. To examine whether purely isolated bacterial strains synthesize an enzyme inhibitor or not, the bacterial strains were inoculated in a test tube (2.4×21 cm) containing 10 mL of the medium for synthesizing an inhibitor (Medium B) described in Table 1 and cultured at 30° C. for 24 hrs in a shaking water bath.

After the culture solution was subjected to centrifugation (10,000×g, 20 min) to isolate a supernatant, the supernatant was used to examine whether the enzyme inhibitor was synthesized or not. The isolated strain was cultured in a medium for storage (Medium C) described in Table 1 and stored at a cold dark room until it was used in the following experiment.

II. Medium and Cultivation

To synthesize an enzyme inhibitor, the isolated strain was inoculated into a test tube (1.5×15 cm) containing 3 mL of Medium B (Table 1) with a platinum loop and pre-cultured in a shaking incubator (120 Rev.×6 cm stroke) at 30° C. for 16 hrs. The pre-cultured strain (100 µl) was inoculated into a shaking flask (500 mL in volume) containing 100 mL of the medium for main culture (Medium B. Table 1) and cultured at 30° C. for 24 hrs in a shaking water bath. Then, the growth and inhibitor synthesis of the bacterial strain were measured.

To prepare a crude enzyme solution of adenosine deaminase originated from a microorganism, *Nocardioides* sp. J-326TK was inoculated in a test tube (1.5×15 cm) containing 3 mL of Medium D (Table 1) with a platinum loop and pre-cultured in a shaking incubator (120 Rev.×6 cm stroke) at 30° C. for 24 hrs. The pre-cultured strains (100 µl) was inoculated in a shaking flask (500 mL in volume) containing 100 mL of Medium D (Table 1) and cultured at 30° C. for 18 hrs in a shaking water bath. Then, the culture solution was subjected to centrifugation (10,000×g, 4° C., 20 min) to isolate a supernatant and the supernatant was used as a crude enzyme solution.

Test Example 1

Preparation of Enzyme Solution and Measurement of Enzyme Activity

I. Methods for Preparing an Enzyme Solution and Measuring an Enzyme Activity

An animal-derived adenosine deaminase used in this experiment was an enzyme extracted from a bovine pancreas followed by freeze-drying. First, the freeze-dried enzyme was dissolved in 3 mL of a potassium phosphate buffer (pH 7.0) to prepare an enzyme solution. 50 µl of the enzyme solution was collected and diluted with the same buffer in a proper ratio and used as an enzyme for an enzyme reaction. Further, a microorganism-derived enzyme was prepared by culturing *Nocardioides* sp. J-326TK in Medium D (Table 1) and centrifuging the culture solution to separate a supernatant. The supernatant thus obtained was used as a crude enzyme solution.

An enzyme activity was measured according to the method described by the Kalckar. Namely, a reaction mixture (final volume: 1.0 mL) comprising 5 µmoles of adenosine, 50 µmoles of a potassium phosphate buffer (pH 7.0) and a proper amount of the enzyme solution were reacted in a water bath at 37° C. for 30 min and then subjected to boiling at 100° C. for 4 min to stop the enzyme reaction. The reaction mixture was diluted 100-fold with the same buffer and its absorbance was measured at 265 nm.

1 Unit of enzyme activity was defined as the amount of an enzyme synthesizing 1 µmole of inosine at the above-mentioned condition for 1 hr.

II. Measurement of Inhibitory Activity of an Adenosine Deaminase Inhibitor

An inhibitory activity of an inhibitor compound was determined by using an inhibition rate which inhibits a deamination reaction of adenosine deamidase. Namely, the inhibition rate was calculated from the difference between an enzyme activity of a standard control and an enzyme activity when an inhibitor was treated. The amount of enzyme for the measurement of an enzyme activity was about 17~26 units/ml, and the concentration of an inhibitor compound was regulated so that the inhibition rate of an adenosine deaminase activity can be 70% or below.

The inhibitory activity of 1 mL sample showing 50% inhibition rate was defined as 1 unit. The inhibition rate and inhibitory activity were calculated as follows.

Inhibition rate=(enzyme activity−sample activity)/ enzyme activity×100(%)

Inhibitory activity=inhibition rate/50×dilution rate (units/mL)

Example 2

Purification of an Adenosine Deaminase Inhibitor

To purify an adenosine deaminase inhibitor, after the culture supernatant was separated by centrifugation, pre-treated with an activated charcoal and extracted with 80% methanol, the extract obtained thus was concentrated under a reduced pressure. The concentrated extract was successively subjected to methanol fraction, Dowex 1X1-100 (Cl—) column chromatography and Dowex 50W-X4 (H$^+$) column chromatography, to collect fractions showing an inhibitory activity. The collected fractions were combined and subjected to Bio gel P2 gel filtration, normal phase TLC and reverse phase TLC, in order.

Test Example 2

Classification and Identification of the Isolated Strain

Morphological, cultural and biochemical features of the isolated strain IADA-7 (KCTC 10446BP) were examined to characterize its taxonomical position, and a classification and identification of the isolated strain IADA-7 (KCTC 10446BP) were carried out according to the methods described in "Bergey's Manual of Bacteriology" (the 8$^{th}$ Edition) and "Bergey's Manual of Systematic Bacteriology" (Vol. 2).

1) Morphological Feature

A morphological experiment of the isolated strain was carried out according to the methods described in "Laboratory Microbiology" (the 3$^{rd}$ Edition), "Classification and identification of microorganism" and "Manual of Methods for General Bacteriology".

The isolated strain IADA-7 (KCTC 10446BP) was inoculated in a nutrient broth agar medium and cultured for 5, 10, 20 and 48 hrs to observe its morphological change according to time course. As shown in Table 2 and FIG. 1 (a length of bar in FIG. 1 is 5 μm), it was found that the isolated strain IADA-7 is a Gram-negative, rod-shaped strain which has a motility and forms a spore.

TABLE 2

| Article | Feature |
| --- | --- |
| Morphology | Rod shape with round end |
| Motility | Motile |
| Gram staining | Positive |
| Spore | Spore forming |

2) Cultural Feature

A gelatin stab medium experiment was performed using a nutrient gelatin stab medium, and a carbohydrate fermentation experiment was carried out according to the method described in "Biochemical Tests for Identification of Medical Bacteria".

As shown in Table 3, the cultural features of the isolated strain IADA-7 (KCTC 10446BP) were characterized that it used glucose, fructose, D-arabinose, maltose and trehalose as a carbon source, but did not use mannitol, xylose, L-arabinose and lactose.

TABLE 3

| Article | Isolated strain (IADA-7) |
| --- | --- |
| D-glucose | + |
| D-mannitol | − |
| D-fructose | + |
| D-xylose | − |
| D-arabinose | + |
| L-arabinose | − |
| L-xylose | − |
| Lactose | − |
| Maltose | + |
| Trehalose | + |
| Sorbitol | − |
| Inoline | − |
| Saccharose | − |

+: use,
−: nonuse

3) Biochemical Feature

The biochemical feature of the isolated strain was analyzed according to the methods described in "Biochemical Tests for Identification of Medical Bacteria" and "Manual of Methods for General Bacteriology".

As a result of examining the biochemical feature of the isolated strain IADA-7 (KCTC 10446BP), as shown in Table 4, it was found that it showed positive signals in a catalase test, gelatin liquefaction and urease test, but a negative signal in a lysine decarboxylase test.

TABLE 4

| Article | Isolated strain (IADA-7) |
| --- | --- |
| Catalse test | + |
| Anaerobic growth | − |
| Indol test | − |
| Gelatin liquefaction | + |
| Lysine decarboxylase | − |
| Ornitine decarboxylase | − |
| Arginine decarboxylase | + |

TABLE 4-continued

| Article | Isolated strain (IADA-7) |
| --- | --- |
| Urease test | − |
| H$_2$S production | − |

4) Classification and Identification of the Isolated Strain

According to the "Bergey's Manual of Systematic Bacteriology" (Vol. 2), most of chemoheterotrophic and catalase-positive strains are belongs to Bacillus sp. As described in the above, the isolated strain IADA-7 (KCTC 10446BP) which was Gram-positive, aerobic, endospore forming rod-shaped strain was identified as Bacillus sp. by examining its cultural and biochemical features and comparing them with those of "Bergey's Manual of Bacteriology" (the 8$^{th}$ Edition) and "Bergey's Manual of Systematic Bacteriology" (Vol. 2).

Consequently, the isolated strain IADA-7 was designated Bacillus sp. IADA-7 and deposited at Korean Collection for Type Cultures (Address: #52, Oun-dong, Yusong-ku, Taejon 305-333, Republic of Korea) on Mar. 18, 2003 under the accession number of KCTC 10446BP, in accordance with the terms of the Budapest Treaty on the International Recognition of the Deposit of Microorganism for the Purpose of Patent Procedure.

Example 3

Examination of a Synthetic Condition of an Adenosine Deaminase Inhibitor

1) Effects of the Amount of Ventilation and Initial pH

The effects of pH and the amount of ventilation on a cell growth and synthesis of an inhibitor compound were examined. As a result, as shown in Table 5, it was found that when it was well ventilated, the cell growth and synthesis of an inhibitor compound were increased. Further, as shown in Table 6, the cell growth was favorable in an alkali pH range rather than an acidic pH range and the inhibitor compound was also synthesized more in the alkali pH range.

TABLE 5

| The amount of medium (mL) | Activity (units/mL) |
| --- | --- |
| 50 | 4,600 |
| 100 | 4,800 |
| 150 | 4,300 |
| 200 | 4,000 |
| 250 | 3,600 |

The medium is composed of glucose 1.0 g, yeast extract 0.2 g, meat extract 0.2 g, peptone 0.2 g, KH$_2$PO$_4$ 0.05 g and MgCl$_2$.6H$_2$O 0.01 g.

TABLE 6

| Initial pH | Activity (units/mL) |
| --- | --- |
| 3 | 400 |
| 6 | 4,300 |
| 7 | 4,900 |
| 9 | 4,600 |

Figure 2:
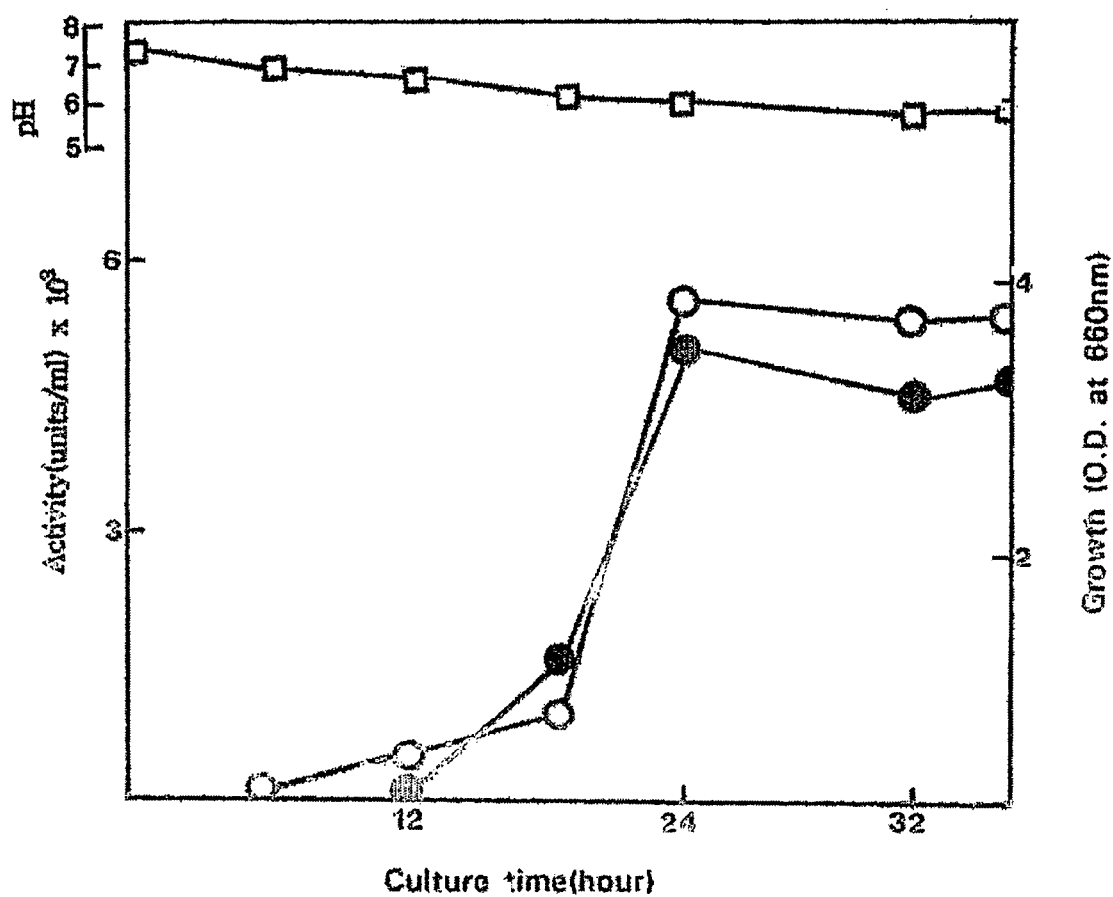
FIG. 2 shows a graph representing a bacterial growth, synthesis of an inhibitor compound and pH variation according to time of culturing the *Bacillus* sp. IADA-7 (KCTC 10446BP) strain of the present invention.

The medium is composed of glucose 1.0 g, yeast extract 0.2 g, meat extract 0.2 g, peptone 0.2 g, KH$_2$PO$_4$ 0.05 g and MgCl$_2$.6H$_2$O 0.01 g 2) Cell Growth and Synthesis of an Inhibitor Cell growth, synthesis of an inhibitor compound and pH variation were measured according to time course of cultivation. As a result, as shown in FIG. 2, it was found that the cell growth was the highest at 24 hrs after the cultivation and the synthesis of an inhibitor compound became slightly decreased after 24 hrs (in FIG. 2, '□' means pH, '○' means a cell growth, and '●' inhibitory activity).

Example 4

Purification of an Adenosine Deaminase Inhibitor

1) Preparation of a Supernatant

After the isolated strain was picked with a platinum loop from a storage slant culture tube and inoculated in a test tube containing 3 mL of a medium for synthesizing an inhibitor, the test tube was incubated at 30° C. for 16 hrs in a shaking water bath. The culture solution (100 μl) was transferred to 500 mL in volume of a shaking flask containing 100 mL of the same medium and cultured at 30° C. for 24 hrs in a shaking water bath.

The culture solution was subjected to centrifugation (10,000×g, 4° C., 20 min) to remove cells, and a supernatant thus obtained was used as a crude inhibitor solution of the adenosine deaminase. Since the supernatant showed 5,100 units per 1 mL of an enzyme activity and a total volume of the supernatant was 8,820 mL, a total activity was 45,000,000 units.

2) Extraction with an Activated Charcoal

After pH of the culture solution (300 mL, 4,500 units/mL, 1,350,000 units) was adjusted to 7.0, 6 g of a dried activated charcoal washed with methanol was added thereto and the reaction mixture was stirred.

After the reaction mixture was subjected to aspiration for 10 min, the activated charcoal on a filter paper was washed with distilled water. The washed activated charcoal was divided into 6 equal parts (225,000 units) and extracted with six kinds of organic solvents by aspiration, respectively (Table 7). As shown in Table 7, since when the activated charcoal was extracted with 80% methanol, the extraction yield was the highest, 200 mL of the concentrated supernatant (7,740,000 units) was divided into 4 equal parts (50 mL; 1,935,000 units) and pH of each supernatant was adjusted to 2, 6, 7 and 8, respectively. Then, each supernatant was subjected to absorption to the activated charcoal and extracted with 80% methanol (Table 8).

TABLE 7

| Solvent | Inhibitory activity (units) | Yield (%) |
|---|---|---|
| 80% methanol | 126,000 | 56 |
| 100% ethanol | 112,500 | 50 |
| 80% butanol | 87,000 | 39 |
| 100% hexanol | 81,000 | 36 |
| 50% chloroform | 69,750 | 31 |
| 50% acetone | 74,200 | 33 |

TABLE 8

| Solvent | pH | Inhibitory activity (units) | Yield (%) |
|---|---|---|---|
| Methanol (80%) | 2 | 619,000 | 32 |
| | 6 | 1,199,700 | 62 |
| | 7 | 1,393,200 | 72 |
| | 8 | 1,470,000 | 76 |

According to the results shown in Tables 7 and 8, after pH of the supernatant was adjusted to 8 during the purification, the activated charcoal (Sigma, 100~400 mesh) was added to the culture solution at a final volume of 2 w/v/% and the reaction mixture was stirred for 10 min. Then, the reaction mixture was subjected to aspiration using an aspirator. After the aspiration, the reaction mixture was washed with the tertiary distilled water twice in a quarter volume of the culture solution and was extracted with the equal volume of 80% methanol to the culture solution four times. The extract was concentrated into a final volume of 100 mL under a reduced pressure and subjected to centrifugation (10,000×g, 30 min) and filtration using a membrane filter having 2 μm in pore size (Disposable sterile syringe filter) to remove the activated charcoal.

Since the activated charcoal extract showed 310,500 units of an enzyme activity per 1 mL and a total volume of the concentrated activated charcoal extract was 100 mL, a total activity was 31,050,000 units and the yield for the supernatant was 69%.

3) Methanol Fractionation

Cold methanol was added to the collected sample extracted with the activated charcoal at a final volume of 50%, and the mixture was kept at a freezer at −20° C. for 24 hrs. After the frozen mixture was subjected to centrifugation (10,000×g, 30 min) to remove a precipitate and methanol was evaporated with a rotary evaporator at 45° C., distilled water was added thereto and its pH was adjusted to 8.0 with 1 N NaOH.

Since the methanol fraction showed 558,000 units of an enzyme activity per 1 mL and a total volume of the methanol fraction supernatant was 50 mL, a total activity was 27,900,000 units and the yield for the supernatant was 62%.

4) Dowex 1X1-100 (Cl—) Ion Exclusive Chromatography

After confirming (+) electric charge with high voltage paper electrophoresis, an ion exclusive chromatography was carried out. The methanol fraction was loaded onto Dowex 1X1-100 (Cl—) column (3.4×37 cm) at a flow rate of 0.25 mL/min and the column was washed with distilled water. Since the concentrate obtained from the Dowex 1X1-100 (Cl—) column showed 462,000 units of an enzyme activity per 1 mL and a total volume of the concentrate was 50 mL, a total activity was 23,100,000 units and the yield for the supernatant was 51%.

5) Dowex 50W-X4 ($H^+$) Ion Exchange Chromatography

Figure 3:
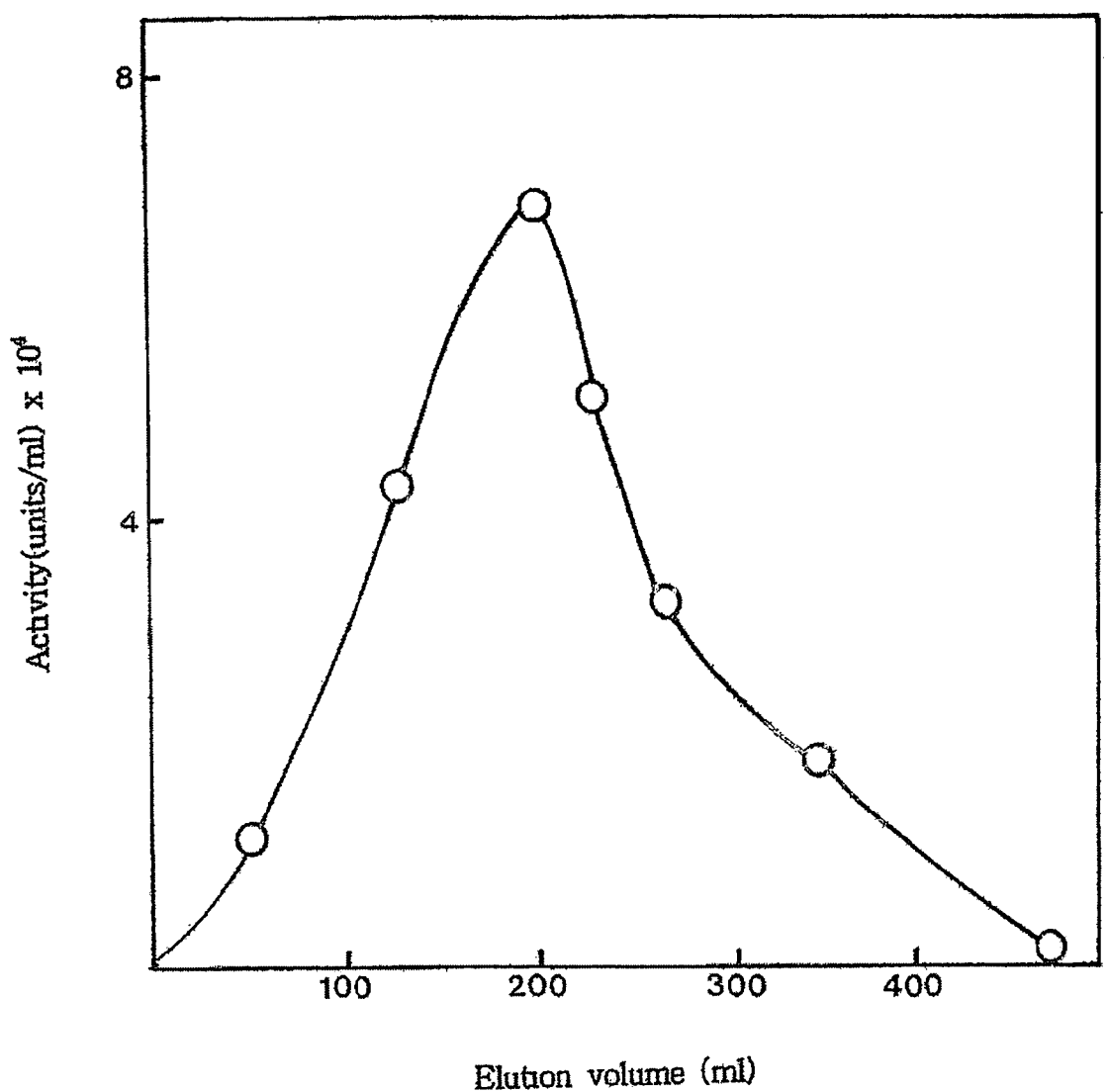
FIG. 3 shows a result of purifying the inhibitor compound of the present invention with Dowex ion exchange resin.

The sample obtained from the Dowex 1X1-100 (Cl—) column was loaded onto Dowex 50W-X4 ($H^+$) column (3.4× 37 cm) at a flow rate of 0.25 mL/min and the column was washed with the tertiary distilled water. An inhibitor compound absorbed to the column was eluted with 0.2 N $NH_4OH$ at a flow rate of 0.25 mL/min (FIG. 3). An effluent was separately distributed by 30 mL, concentrated under a reduced pressure, and then, its activity was measured.

As shown in FIG. 3, fractions 1 to 3 and after 8 were discarded because they showed a tailing and low productivity of the inhibitor compound, and fractions 4 to 7 were concentrated under a reduced pressure to make 30 mL of an effluent.

Since the concentrate of fractions 4 to 7 obtained from the Dowex 50W-X4 ($H^+$) ion exchange chromatography showed 37,000 units of an enzyme activity per 1 mL and a total volume of the concentrate was 30 mL, a total activity was 7,100,000 units and the yield for the supernatant was 15%.

6) Bio-Gel $P_2$ Gel Filtration

Figure 4:
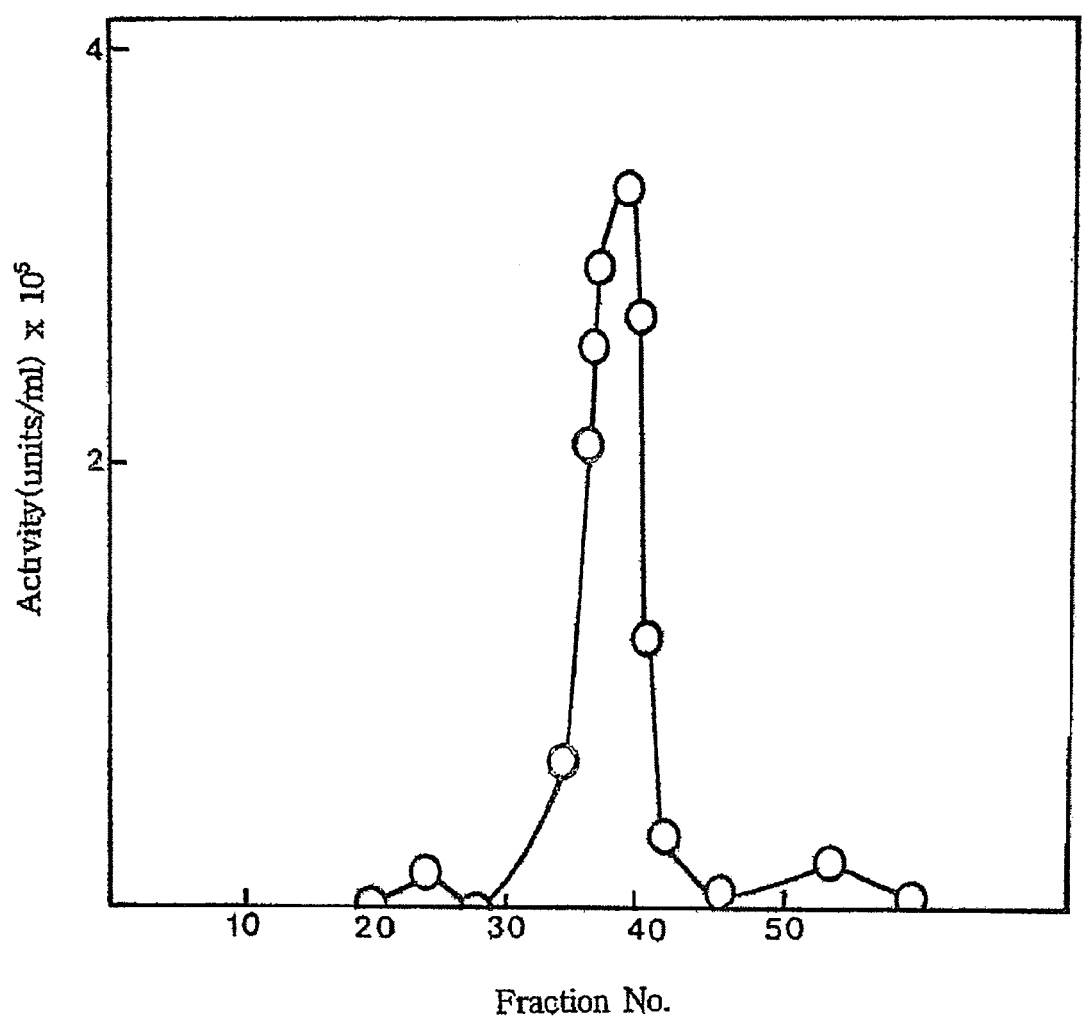
FIG. 4 shows a result of purifying the inhibitor compound of the present invention with a gel filtration.

Fractions 4 to 7 obtained from Dowex 50W-X4 (H+) ion exchange chromatography were collected and concentrated into 2 mL under a reduced pressure. The concentrate was loaded onto Bio-gel $P_2$ column (1.6×48 cm) and fractionated by 3 mL with the tertiary distilled water at a flow rate of 0.18 mL/min. Elution profiles of each sample are shown in FIG. 4.

Since the concentrate of fractions 35 to 39 obtained from the gel filtration showed 225,000 units of an enzyme activity per 1 mL and a total volume of the concentrate was 10 mL, a total activity was 2,250,000 units and the yield for the supernatant was 5%.

7) Reverse Phase TLC

Thin layer chromatography (TLC) has the advantages over paper chromatography that it can save the time for developing, efficiently carry out the development, and detect a very small amount of a compound because the compound becomes concentrated onto a spot. Since normal phase TLC employs a polar substance as a stationary phase, it has a demerit that a tailing is often occurred when the polar substance is loaded thereon. Therefore, the present invention used reverse phase TLC which uses a non-polar substance as a stationary phase.

Fractions 35 to 39 obtained from Bio-gel $P_2$ gel filtration were collected and concentrated into 2 mL under a reduced pressure. The concentrated sample was dropped on a reverse phase-$18F_{254}$ plate (20×20 cm) and developed in an solvent system ($NH_4Cl$:ethanol:water=6:4:1 (v/v/v)).

The development of an inhibitor compound was examined under UV irradiation. Then, silica gels positioned at 0.3 cm up and down from $R_f$=0.85 were scratched from the paper and eluted with methanol. The extract was concentrated under a reduced pressure to remove methanol, and then, the concentrated sample was dissolved in 2 mL of HPLC water.

8) Normal Phase TLC

The sample (2 mL) obtained from reverse phase TLC was dropped on a silica gel G-60 plate (20×20 cm) and developed in an solvent system (chloroform:methanol=7:3, v/v). To confirm the development of an inhibitor compound, a piece of paper severed from left and right ends of the developing paper by 2 cm was steamed with iodine vapor. Then, silica gels positioned at 0.3 cm up and down from $R_f$=0.35 were scratched from the paper and eluted with methanol. The extract was concentrated under a reduced pressure to remove methanol, and then, the concentrated sample was dissolved in 2 mL of HPLC water.

Generally, when the silica gel scratched from TLC is eluted, the silica gel remains in an effluent, which makes difficult a complete purification. To solve this problem, the present invention carried out centrifugation (10,000×g, 30 min) and filtration using a membrane filler having 0.2 μm in pore size. After sufficiently packing a cotton wool in a column (1×7 cm) at first, Dowex 1X1-100 (Cl—) resin was packed thereon and eluted with 0.2 N ammonium solution at a flow rate of 0.25 mL/min. Then, the eluted sample was freeze-dried.

The overall procedure was summarized in FIG. 5. An inhibitor compound produced by *Bacillus* sp. IADA-7 (KCTC 10446BP) was purified from the culture solution in a yield of about 2% which corresponds to a dry weight of 9.6 mg.

Experimental Example 3

Confirmation of Purity of an Adenosine Deaminase Inhibitor

1) Normal Phase TLC

Figure 6:
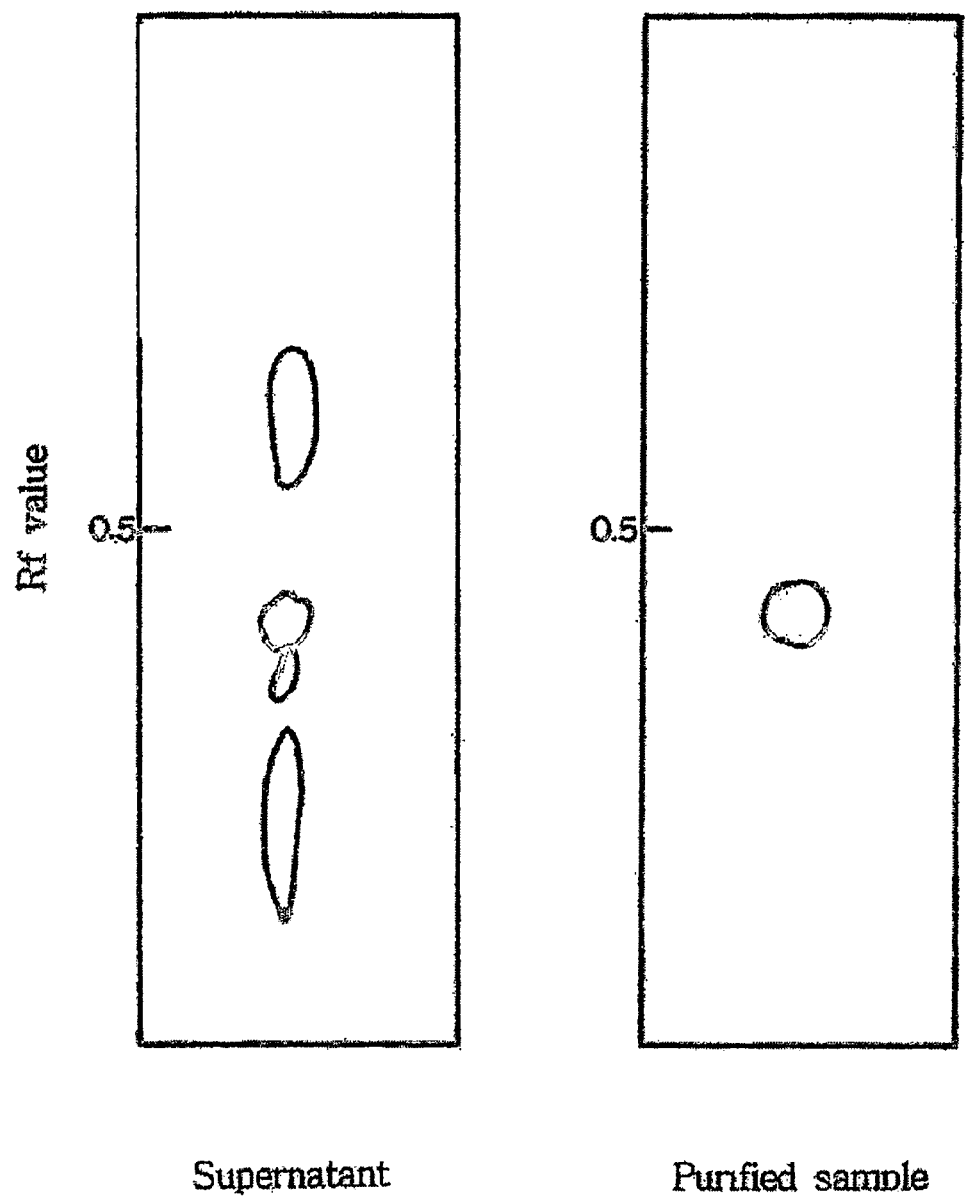
FIG. 6 shows a result of developing the inhibitor compound of the present invention on a normal phase TLC.

The purified sample was loaded onto a silica gel G-60 plate to examine its purity and developed in an solvent system (chloroform:methanol=7:3, v/v). A single spot was detected by steaming with iodine vapor and its result was shown in FIG. 6. As shown in FIG. 6, the single spot was detected at a position of $R_f$=0.35.

2) Reverse Phase TLC

Figure 7:
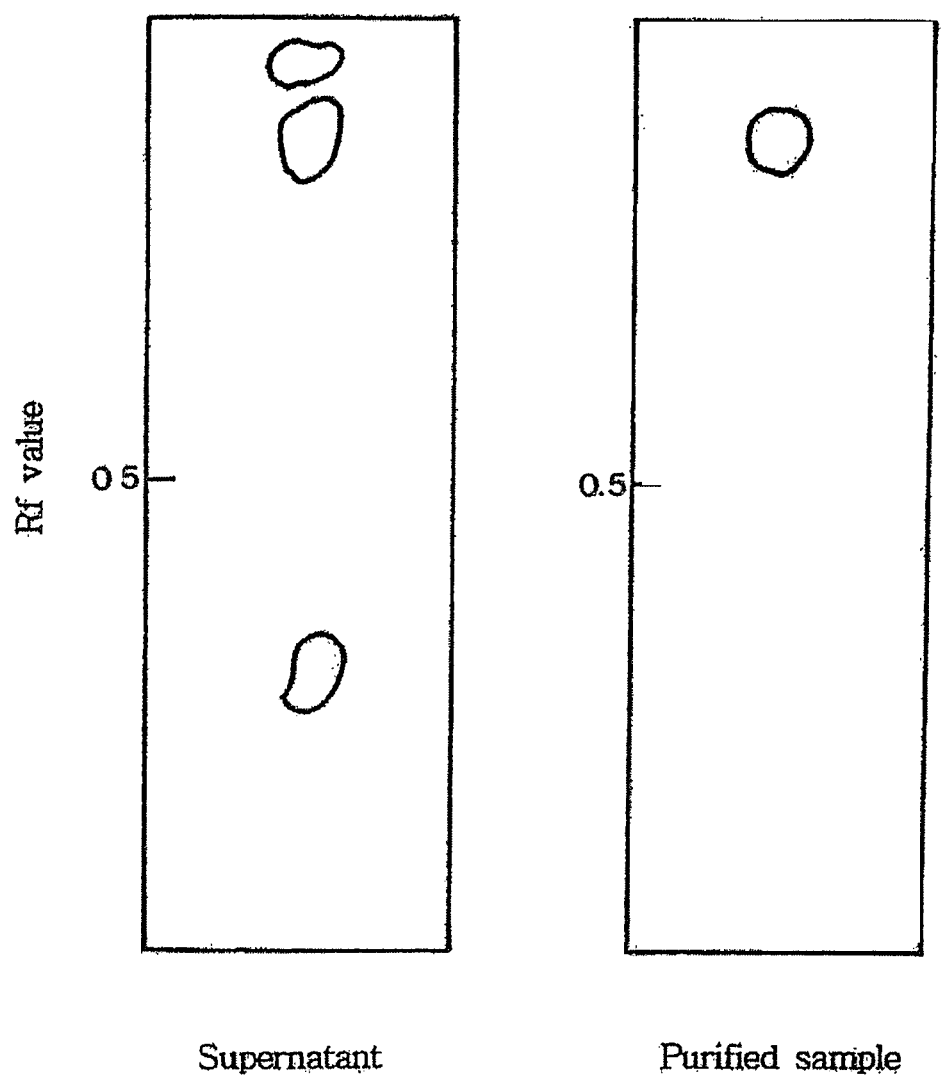
FIG. 7 shows a result of developing the inhibitor compound of the present invention on a reverse phase TLC.

The purified sample was loaded onto a reverse phase-$18F_{254}$ plate and developed in an solvent system ($NH_4Cl$:ethanol:water=6:4:1 (v/v/v)). After a spot was detected by UV, a single spot was detected by steaming with iodine vapor and its result was shown in FIG. 7. As shown in FIG. 7, the single spot was detected at a position of $R_f$=0.85.

3) High Voltage Paper Electrophoresis

Since when a micromolecule substance is isolated by low voltage paper electrophoresis, diffusion occurs too fast, the present invention has used high voltage paper electrophoresis. However, since heat is generated due to high voltage, it is positively necessary to use a cooling system.

Paper electrophoresis was carried out according to the method described by Teintze et al.

Figure 8:
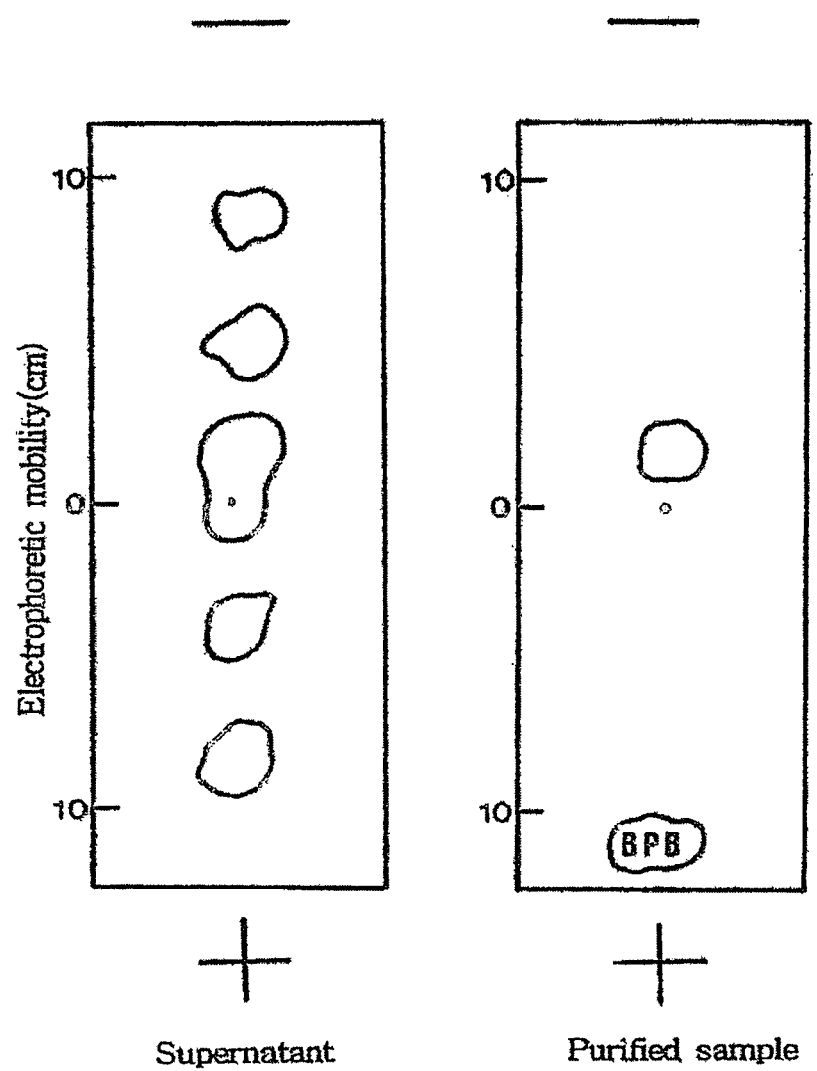
FIG. 8 shows a result of loading the inhibitor compound of the present invention to high voltage paper electrophoresis.

After a paper electrophoresis kit was filled with a potassium phosphate buffer (pH 7.0, 0.02 M), the both ends of Whatman No. 1 paper were soaked in the buffer for 7 hrs to be saturated. The purified sample (20 μl, 90 units/mL) was spotted at a start point of the saturated paper and subjected to electrophoresis at 300 V, 40 A. Then, after drying the paper, it was steamed with iodine vapor to detect a single spot. The result was shown in FIG. 8. As a result of presenting the extent of an electric charge as an absolute value by using bromophenol blue (BPB) as a control, $R_f$ value was 0.13.

4) HPLC (High Performance Liquid Chromatography)

It has been recently developed a hard gel type of carriers such as fine polyvinyl-based lipophilic polymers, porous silica and porous polymers, which show a fast flow rate and resistance to high pressure and have about 10 μm in diameter of a gel particle, and used for a HPLC purification.

Since when a polar substance is isolated using a reverse phase column, its separation efficiency increases, the present invention used Nova pak™ $C_{18}$ column (Waters).

Figure 9:
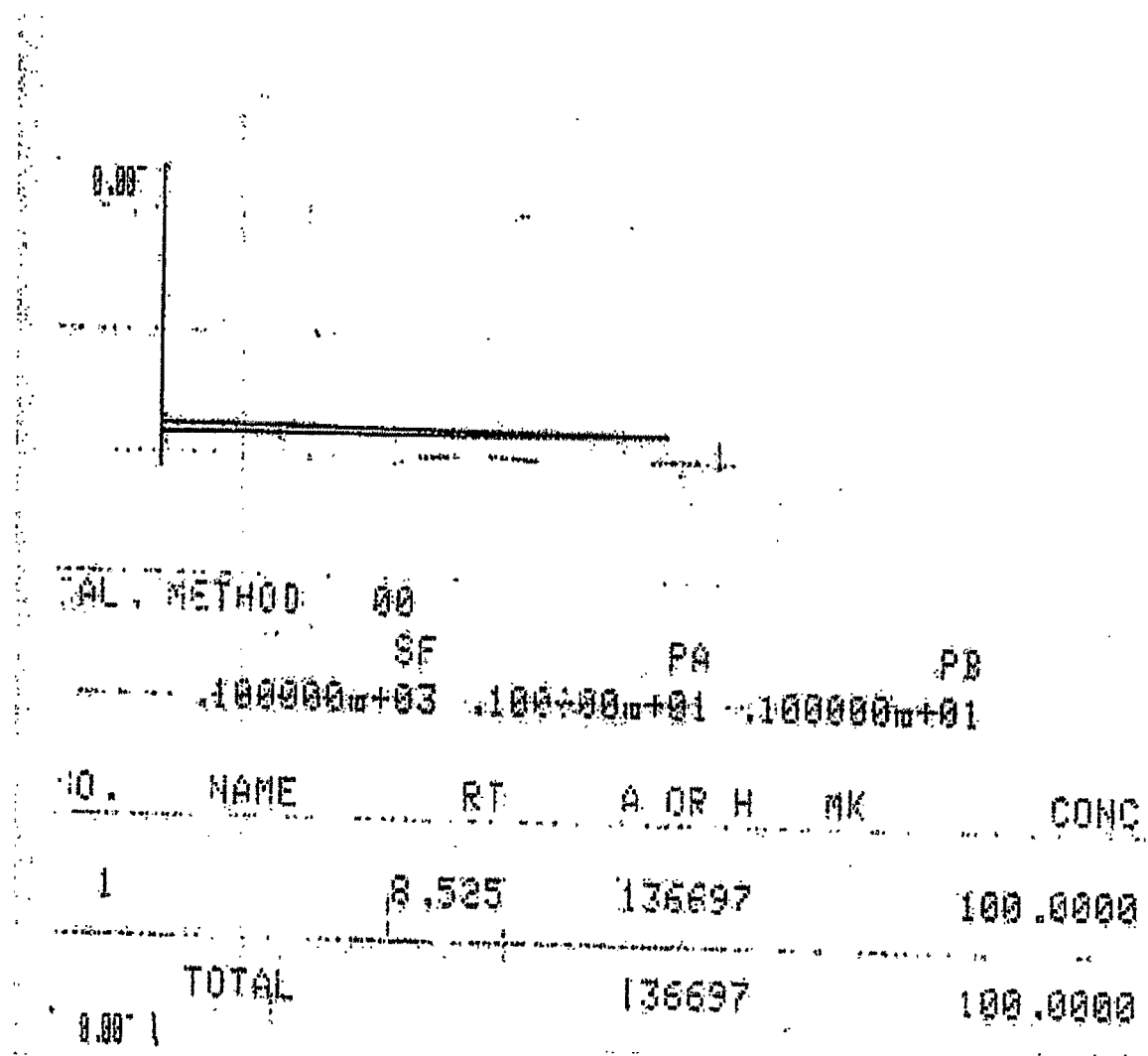
FIG. 9 shows a result of analyzing the inhibitor compound of the present invention with HPLC.
Figure 10:
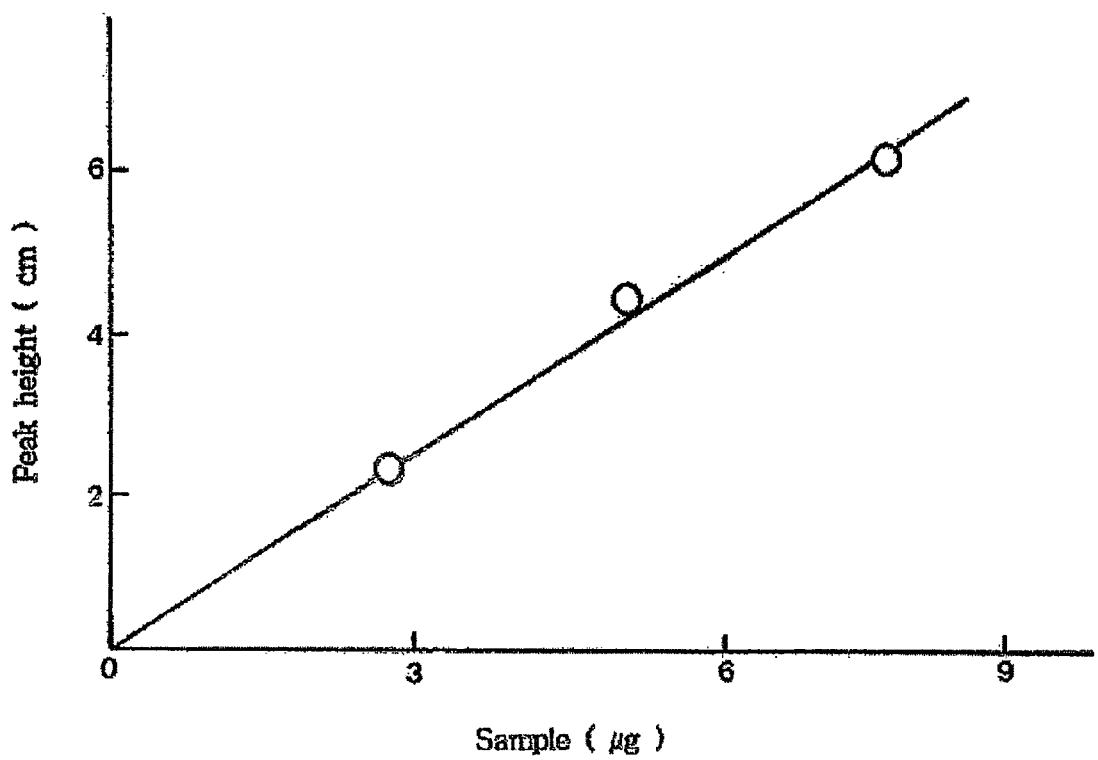
FIG. 10 shows a graph representing the relationship between each peak height and an injection amount in HPLC analysis of the inhibitor compound of the present invention.

The purified sample which was detected as a single spot in normal phase TLC, reverse phase TLC and high voltage paper electrophoresis was subjected to HPLC using Nova pak™$C_{18}$ column. At this time, a flow rate was 0.8 mL/min, HPLC water was used as a solvent, and UV detector 441 was used as a detector. As shown in FIG. 9, a sharp single peak was detected at RT=8.5 min. FIG. 10 showed the relationship between the amount of the purified sample injected and a height of each peak.

As shown in FIG. 10, a linear relationship was shown between the injection amount and a peak's height, which makes possible of quantitatively analyzing by measuring the peak's height.

As shown in the above, since the purified sample was detected as a single spot in normal phase TLC, reverse phase TLC and high voltage paper electrophoresis, and as a single peak in HPLC analysis, it was regarded that the sample was completely purified, and therefore, the sample was freeze-dried and subjected to the following structural analysis.

Test Example 4

Measurement of a Molecular Weight of an Adenosine Deaminase Inhibitor

Figure 11:
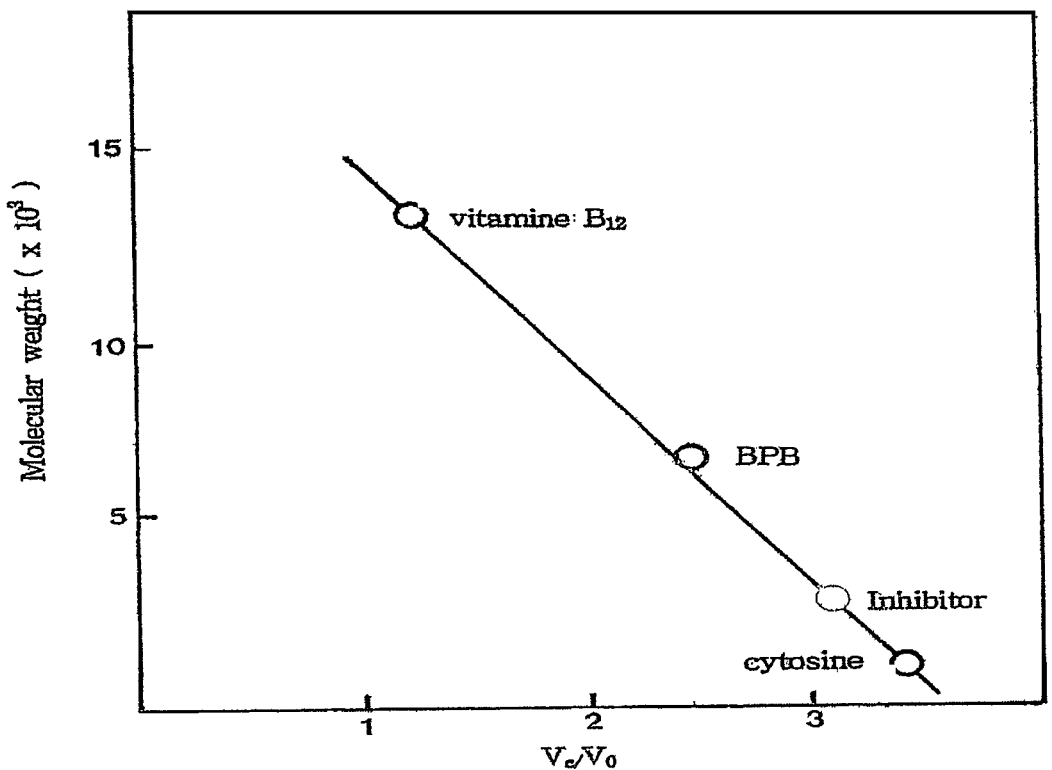
FIG. 11 shows a result of determining a molecular weight of the inhibitor compound of the present invention.

To measure a molecular weight of the sample purified in the above step, the sample was subjected to gel filtration using Bio-gel $P_2$ column (1.6×48 cm). Vitamin $B_{12}$ (M.W. 1,335), BPB (M.W. 669) and cytosine (M.W. 110) were used as a standard control, and the result was shown in FIG. 11. The ratio (Vo/Ve) of an elution volume to a void volume (Vo) was plotted to a logarithmic value of a molecular weight of the standard control. The void volume was determined as the elution volume of hemoglobin (M.W. 64,000).

Vo/Ve of vitamin $B_{12}$ (M.W. 1,335) was 3.3, that of BPB (M.W. 669) was 2.6, that of cytosine (M.W. 110) was 3.3, and that of the inhibitor compound of the present invention was 3.1. Accordingly, the molecular weight of the inhibitor compound was determined as about 175.

Experimental Example 1

Inhibition Mode of an Adenosine Deaminase Inhibitor

Figure 12:
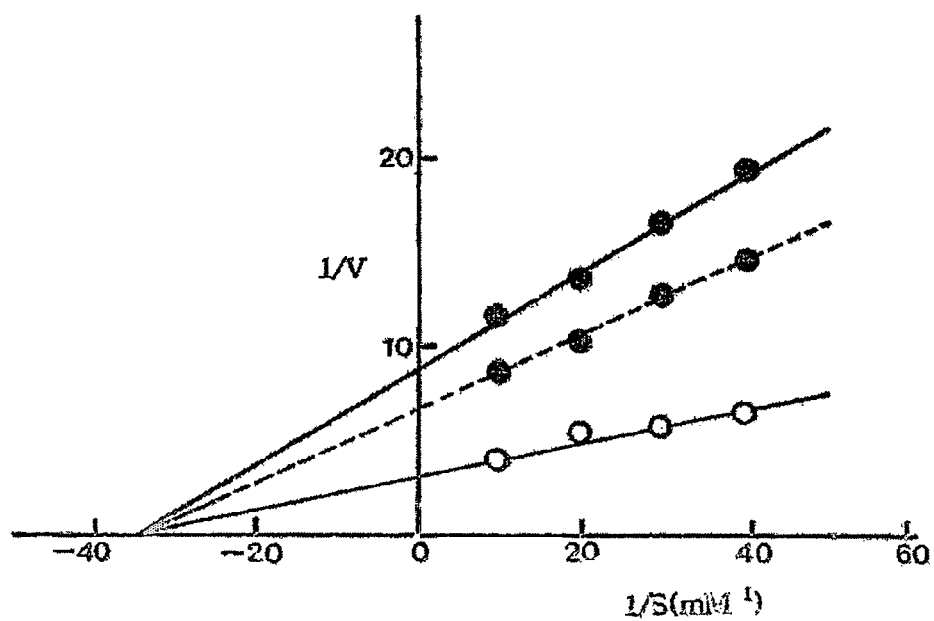
FIG. 12 shows a graph representing a competitive inhibition of the inhibitor compound of the present invention to the adenosine deaminase derived from *Nocardiodes* sp.
Figure 13:
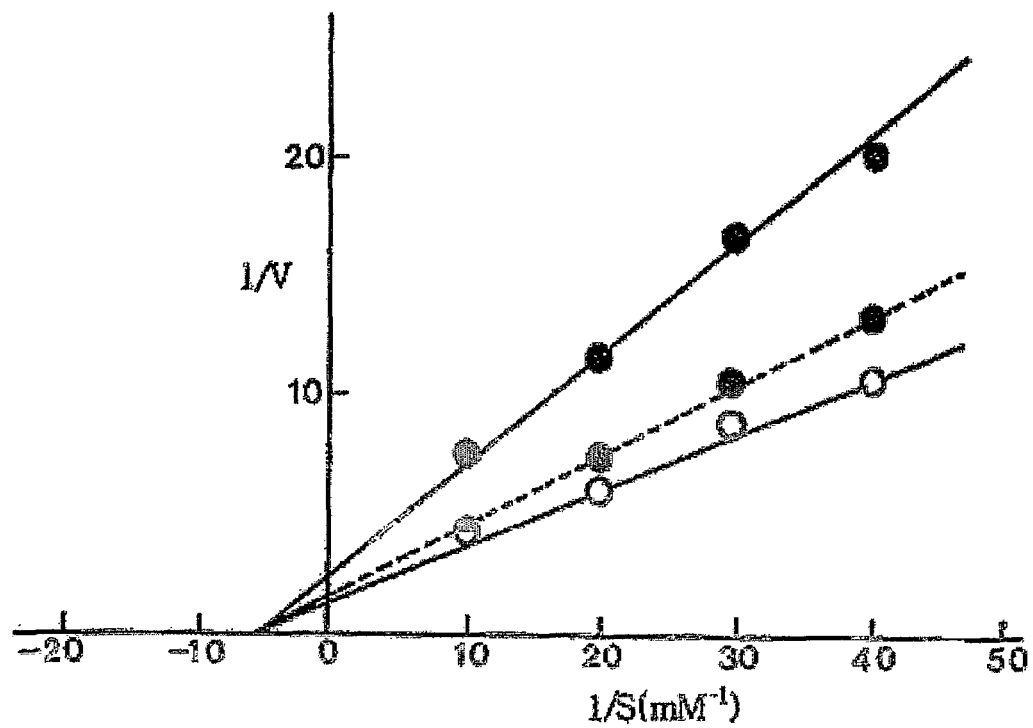
FIG. 13 shows a graph representing a competitive inhibition of the inhibitor compound of the present invention to the adenosine deaminase derived from bovine pancreas.

The effect of an adenosine concentration on adenosine deaminases purified from bovine pancreas and *Nocardiodes* sp. J-326TK cell, respectively, was measured from a Lineweaver and Burk plot. As shown in FIGS. 12 and 13, Km value of the animal-derived enzyme was 0.027 mM, and that of the microorganism-derived enzyme was 0.2 mM. Ki values of 0.01 and 0.02 mg of the purified inhibitor compound to the animal- and microorganism-derived enzymes, respectively, were also measured from a Lineweaver and Burk plot. As shown in FIGS. 12 and 13, Ki value of the animal-derived enzyme was 0.027 mM, and that of the microorganism-derived enzyme was 0.2 mM. (in FIGS. 12 and 13, -○-, --●-- and -●- represents 0, 0.01 and 0.02 mg of the inhibitor compound, respectively).

Like the results described above, since Km value was identical to Ki value and Vmax value decreased as the concentration of the inhibitor compound increased from 0.01 mg to 0.02 mg.

Test Example 5

Physicochemical Property of an Adenosine Deaminase Inhibitor

1) Stability Test

As a result of measuring a residual activity after pH of the culture solution was adjusted to 2, 7 and 9, respectively, and kept at 70° C. for 30 min, it was stable in an alkali pH range (Table 9). Further, as a result of examining the condition for concentrating the culture solution using a rotary vacuum evaporator, it was found that the inhibitor compound of the present invention didn't lose its activity when subjected to the concentration at 45° C. for a long time.

TABLE 9

| Incubation | Residual activity (units/mL) | Relative activity (%) |
| --- | --- | --- |
| pH 2 | 2,900 | 7 |
| pH 7 | 19,500 | 93 |
| pH 9 | 21,000 | 100 |

From the results described in the above, it was found that the inhibitor compound of the present invention was very stable around at room temperature. Accordingly, the purified sample was adjusted its pH to 8 and stored at low temperature of about 5° C.

2) UV Absorption Spectrum

Figure 14:
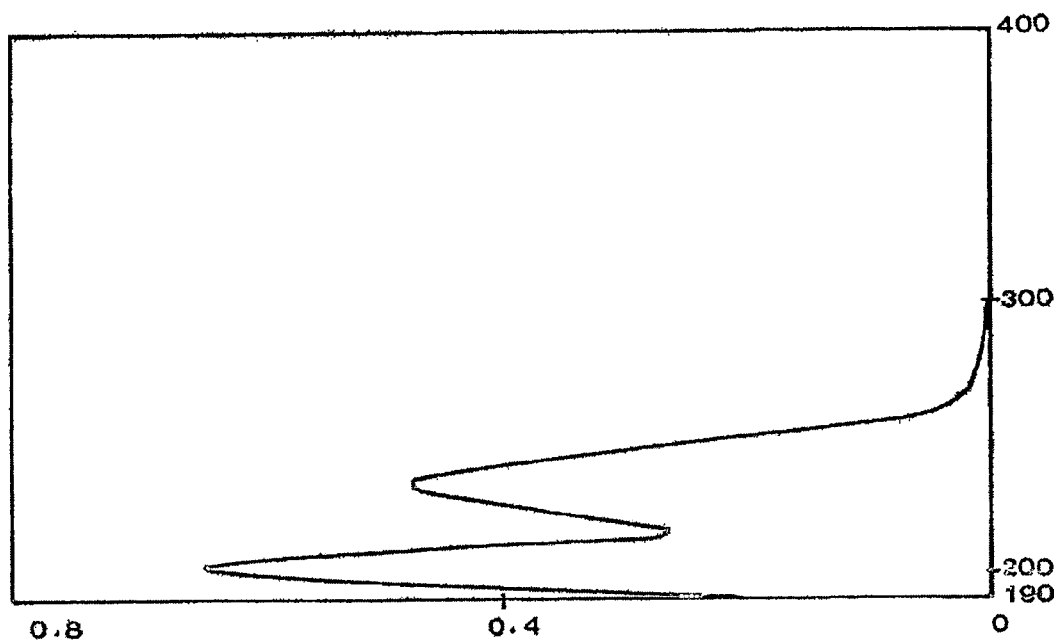
FIG. 14 shows UV absorption spectrum of the inhibitor compound of the present invention.

As shown in FIG. 14, UV absorption spectrum of the purified sample dissolved in milipore water showed the maximum peak at 232 nm and didn't show any peak at a visible range (in FIG. 14, a horizontal line represents OD value and the vertical line represents an absorbance (nm)).

Since IR spectrum 1669 cm$^{-1}$ showed the absorbance of an acetamide and C=O was observed at 192 ppm of $^{13}$C-NMR spectrum, it was predicted that the inhibitor compound of the present invention has the acetamide group. Since the acetamide shows the maximum peak at 220 nm, and when a carbonyl-containing compound bound to the acetamide, the maximum peak may be changed (transition) into 232 nm, it was estimated that the IR spectrum was identical to the NMR spectrum.

3) IR Spectrum

A molecule has a unique oscillation frequency. When the molecule is applied infrared radiation with successively changing a wavelength, the infrared radiation equal to the unique oscillation frequency of the molecule is absorbed, and accordingly, a spectrum according to the molecular structure is obtained. To analyze the molecular structure from the spectrum is an infrared absorption spectroscopy method.

The purified sample (2 mg) was sufficiently ground four times with adding 50 mg of KBr powder per once (total 200 mg). This grinding step was carried out in a dry box to prevent from absorbing water. The ground sample was transferred to an oil pressure processor and slowly pressurized to make a disk. The disk was subjected to FT-IR at 8 cm$^{-1}$ of a resolution and 32 scans of a scanning number, and the result was shown in FIG. 15.

Figure 15:
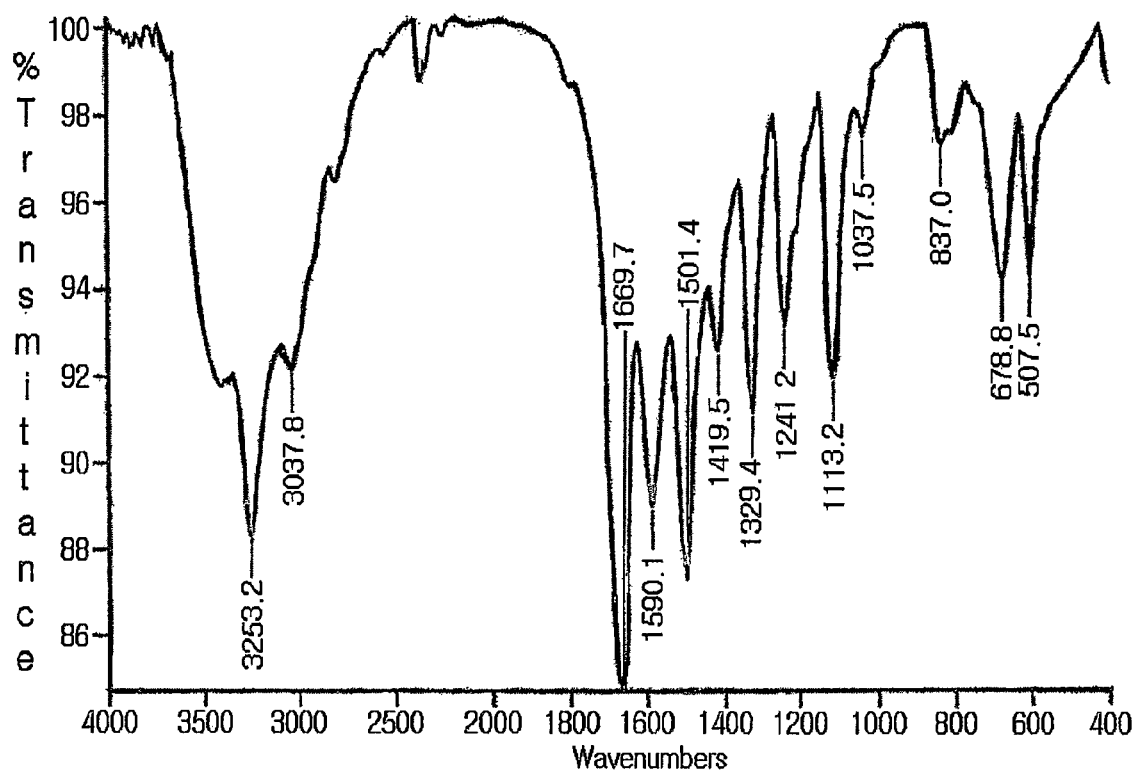
FIG. 15 shows IR absorption spectrum of the inhibitor compound of the present invention.

As shown in FIG. 15, the adenosine deaminase inhibitor compound of the present invention showed an acetamide peak at 1669 cm$^{-1}$ and a pyrol peak at 3037 cm$^{-1}$.

4) $^1$H-NMR Spectrum

Two types of spins, i.e., +½ and −½H, are existed in an atomic is nucleus of H. When this nucleus is put on a magnetic field, each spin originates toward a different energy level. When electromagnetic waves having a resonance frequency are irradiated thereto, +½ type of the spin changes into −½ type of the spin due to energy absorption. To find a molecular structure by detecting this frequency is a NMR spectrum method.

Figure 16:
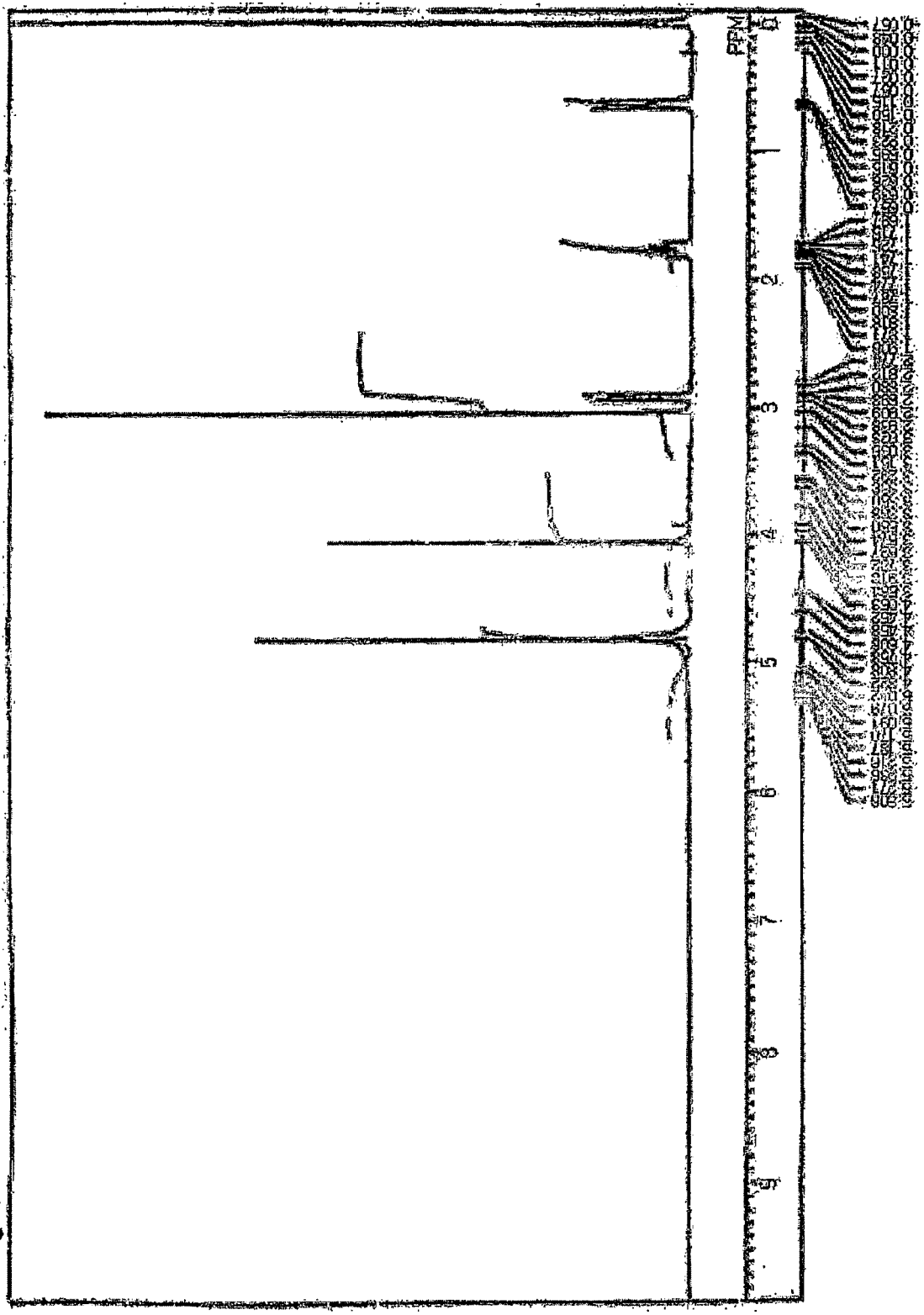
FIG. 16 shows $^1$H-NMR spectrum of the inhibitor compound of the present invention.

The purified sample (2 mg) dissolved in $D_2O$ was filled in a test tube up to 38 mm and subjected to NMR analysis. 500 MHz NMR spectrum was shown in FIG. 16.

5) $^{13}$C-NMR Spectrum

When $^{13}$C nucleus is put on a magnetic field, it divides into +½ and −½ of energy levels and +½ type of the low energy level more exists than −½ type at a thermal equilibrium state. When electromagnetic waves having a resonance frequency are irradiated thereto, +½ type of the nucleus changes into −½ type of the nucleus. When +½ type of the nucleus becomes decreased due to a continuous irradiation, and finally, the number of +½ type of the nucleus is equal to that of −½ type of the nucleus, an absorption does not occurred further and this state is called a saturation.

Figure 17:
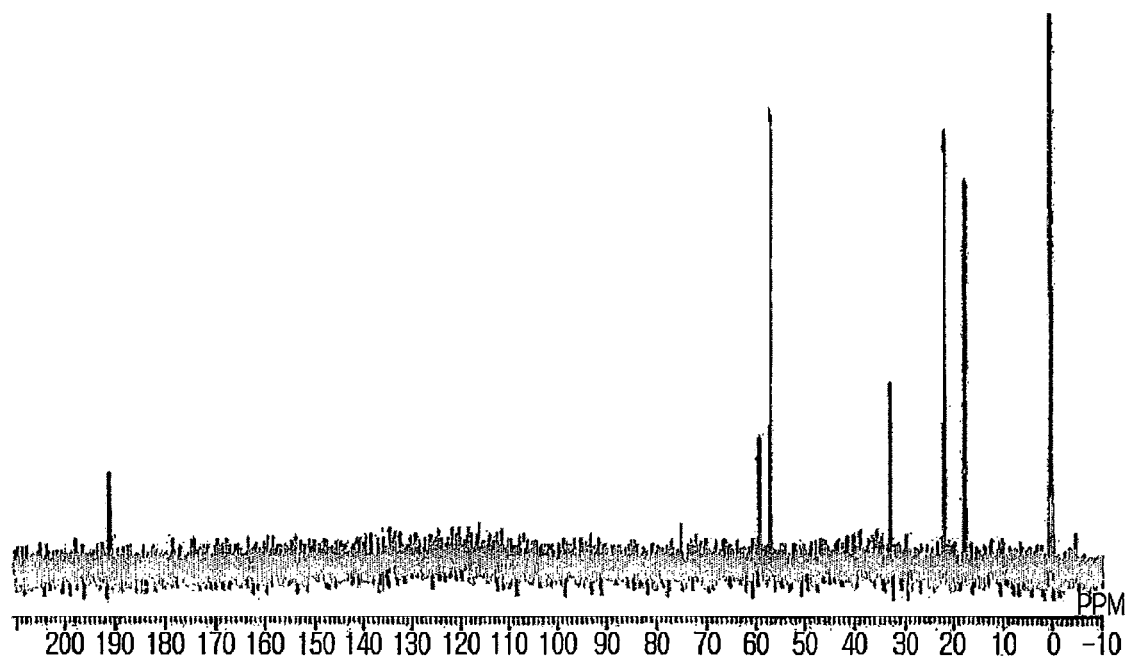
FIG. 17 shows $^{13}$C-NMR spectrum of the inhibitor compound of the present invention.
Figure 18:
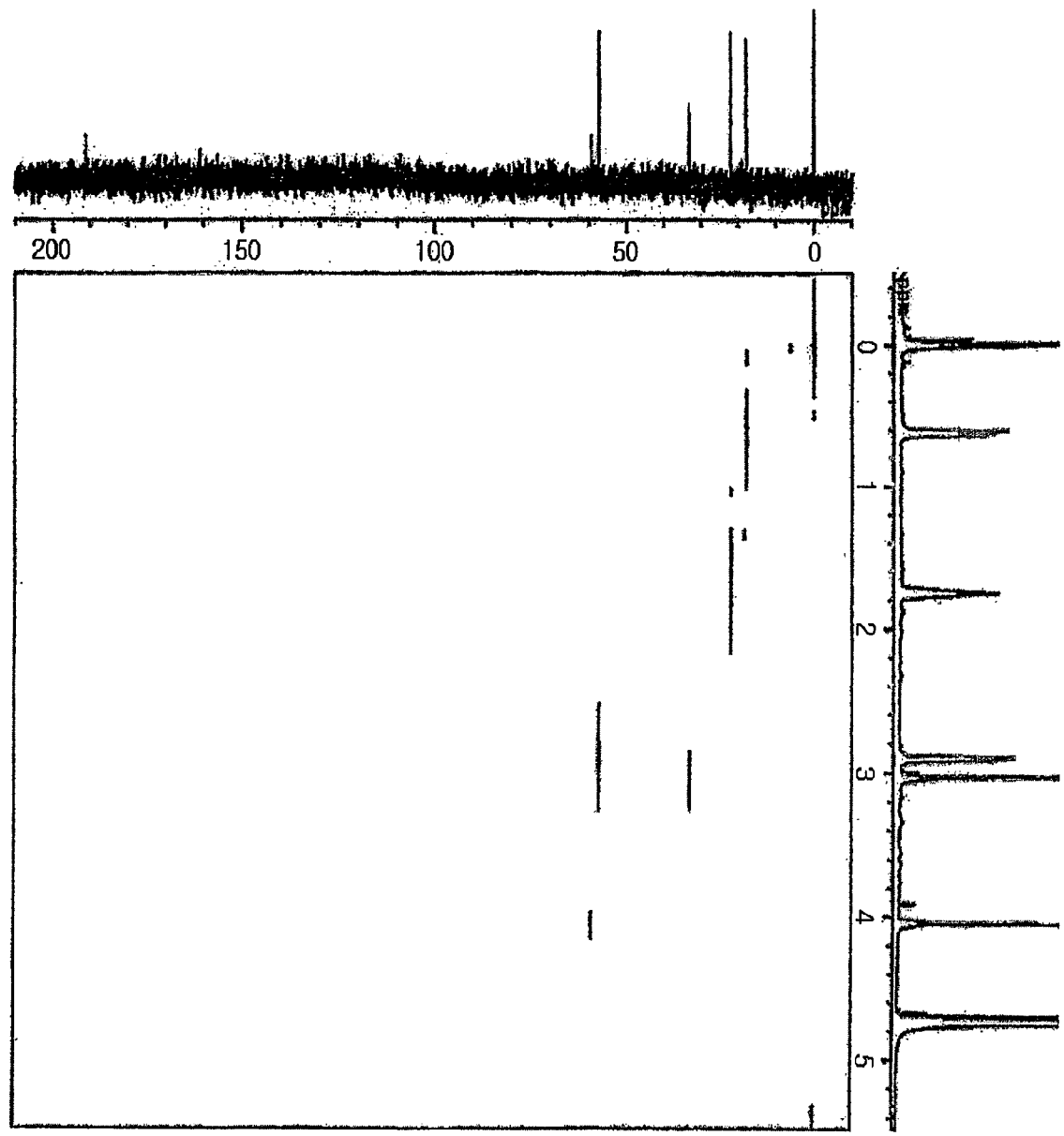
FIG. 18 shows $^{13}$C-NMR spectrum of the inhibitor compound of the present invention.

The spectrum obtained by dissolving 10 mg of the purified sample in $D_2O$ and filling in a microcell capillary of 10 mm in outside diameter and 180 mm in length was shown in FIG. 17. Further, $^{13}$C-H NMR spectrum was shown in FIG. 18.

6) GC-MASS Spectrum

When a sample molecule vaporized by heating in a high-degree vacuum is applied a large energy such as an electron flow, one electron is deviated from the molecule, which results in generating a cationic radical of the molecule (M$^+$, molecular ion). This radical is opened again, to generate several ions called a fragment ion. An equipment for separating and recording these ions according to the ratio (m/e) of a mass (m) and an electric charge (e) is a quantitative analyzer, and the spectrum obtained therefrom is called MASS spectrum. There are two kinds of MASS, i.e., EI-MASS and CI-MASS. The present invention used EI-MASS.

Figure 19:
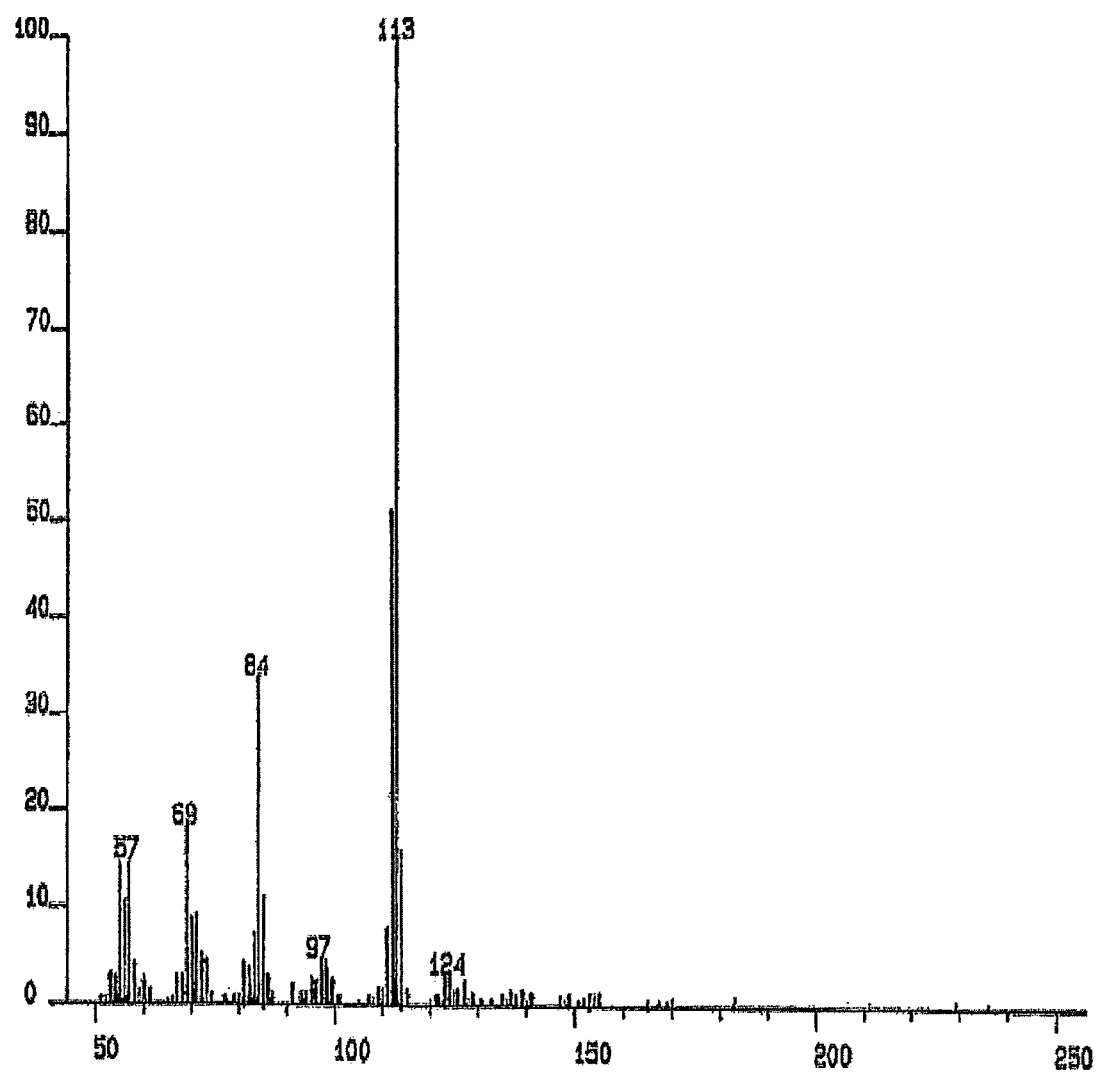
FIG. 19 shows EI-MASS spectrum of the inhibitor compound of the present invention.

The spectrum obtained by dissolving the purified sample in $D_2O$ was shown in FIG. 19, and the molecular weight of the inhibitor compound of the present invention was measured as 124.

7) Structural Analysis

Figure 20:
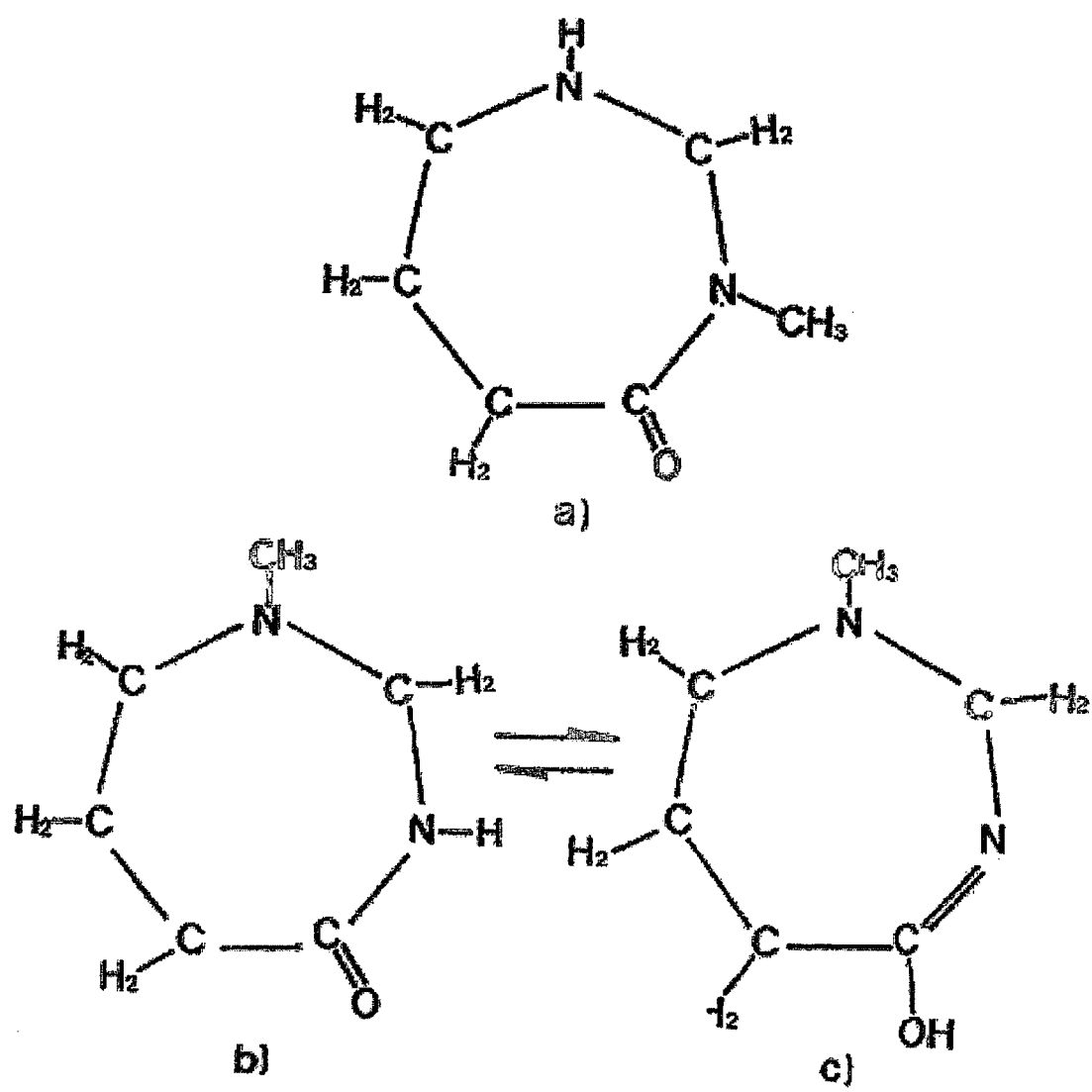
FIG. 20 shows a structural formula of the inhibitor compound of the present invention.

As a result of analyzing the inhibitor compound of the present invention with UV absorption spectrum, IR spectrum, $^1$H-NMR spectrum, $^{13}$C-NMR spectrum, $^{13}$C-$^1$H NMR spectrum and GC-MASS spectrum, it was possible to predict the structure of the inhibitor compound into three types as shown in FIG. 20.

An acetamide group was detected at IR spectrum 1669 $cm^{-1}$ and C=O was observed at $^{13}$C-NMR spectrum 192 ppm, which means that the inhibitor compound contained the acetamide group. Since UVmax of the acetamide group was 220 nm, and when the other molecule bound thereto, the UVmax may be changed into 232 nm, IR spectrum was identical to UV spectrum. Further, the result of comparing $^{13}$C-$^1$H NMR spectrum was shown in Table 10.

TABLE 10

| $^{13}$C-$^1$H NMR spectrum | Analytic result |
|---|---|
| 12-18 (ppm) | $CH_2$ |
| 23-23 | $CH_2$ |
| 34-38 | $CH_3$ |
| 57 | $CH_2$ |
| 59 | —C— |
| 75 | impurities |
| 192 | C=O |

As shown in Table 10, it was found that the inhibitor compound of the present invention was a heterocyclic compound.

Experimental Example 2

Antibacterial Activity Test

To test an antibacterial activity of the inhibitor compound of the present invention, Gram-positive strain *Staphylococcus aureus* and Gram-negative strain *Escherichia coli* were cultured at 37° C. incubator for 18 hrs, 100 µl of each culture solution was densely spread onto a LB agar plate with a platinum loop, and then, cultured at 37° C. incubator for 18 hrs.

When a disc was put on the surface of each incubated plate and 100 units of the inhibitor compound of the present invention was inoculated to the disc, antibacterial rings of 11 mm and 15 mm in diameter was formed at the both plates of *Staphylococcus aureus* and *Escherichia coli*, respectively.

Experimental Example 3

Cytotoxicity of Inhibitor to Human Cancer Cell (1)

Cytotoxicity was measured according to modified MTT assay described by Mosmann with a proper modification. Human transitional-cell carcinoma J82 cells derived from a testis (bladder) were suspended in a serum-free RPMI 1640 medium and PBS (phosphate-buffered saline; KCl 0.2 g, $KH_2PO_4$ 0.2 g, NaCl 8.0 g, $Na_2HPO_4$ 1.15 g, $MgCl_2.6H_2O$ 0.101 g/L, pH7.4) and distributed at a well plate in the amount of 100 µl per well. The concentration of the purified inhibitor compound was adjusted to 0.1, 1 and 10 µg/mL, respectively, and 20 µl each of the inhibitor compound was added to the well plate. At this time, the equal volume of water was used as a control. The well plate was incubated at 37° C., 5% $CO_2$ for 3 days, and the extent of cytotoxicity was determined by using an absorbance measured at 650 nm. The result was shown in FIG. 21.

Figure 21:
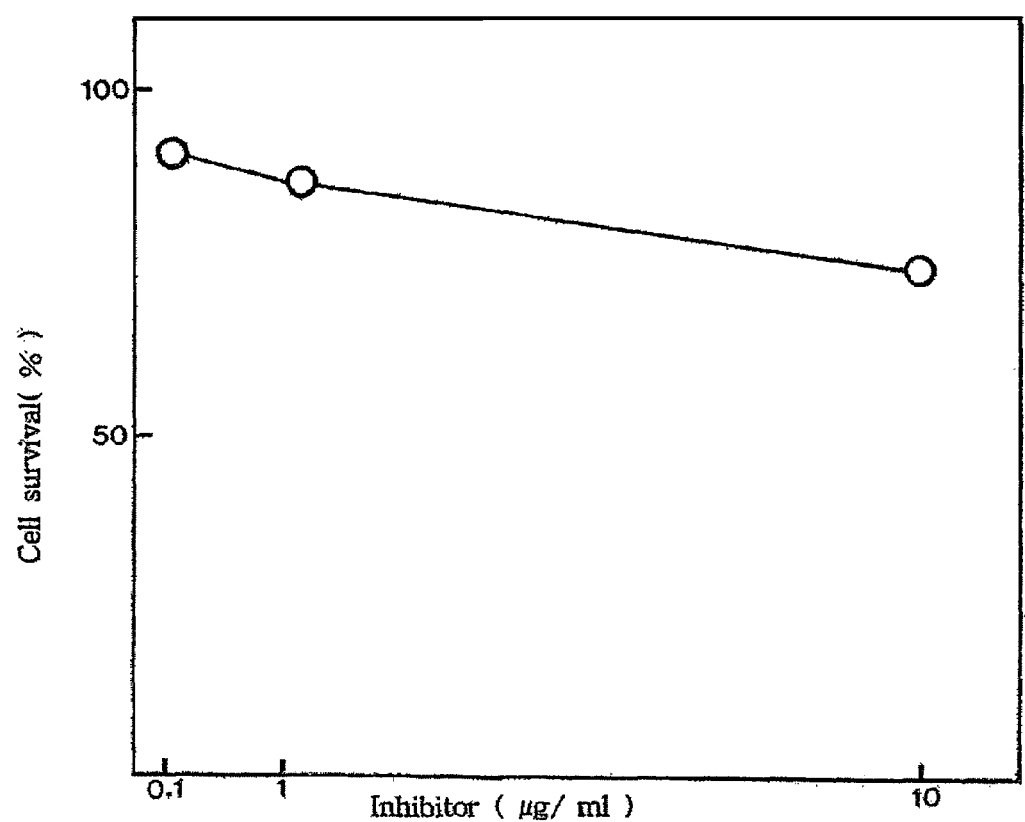
FIG. 21 shows a result of examining cytotoxicity of the inhibitor compound of the present invention to a human transitional-cell carcinoma (bladder) derived from a testis.

As shown in FIG. 21, OD values of each plate added with water (control), 0.1, 1 and 10 µg/mL of inhibitor were 1.100, 0.950, 0.919 and 0.893, respectively. Accordingly, the inhibitor compound of the present invention showed about 19% of cytotoxicity at a concentration of 10 µg/mL.

Experimental Example 4

Cytotoxicity of Inhibitor to Human Cancer Cell (2)

Cytotoxicity was measured according to MTT assay described by Mosmann, and a human leukemia cancer cell, Jurkat T cell was used as a target cell.

When the concentration of the inhibitor compound of the present invention was 40 µg/mL, 50% of cells died, thus showing that $IC_{50}$ of the inhibitor compound is about 40 µg/mL.

From the results described in the above, it was found that the compound of Formula 1, which was isolated from the novel *Bacillus* sp. IADA-7 strain, can be effectively used as an adenosine deaminase inhibitor having high antibacterial and anticancer activities.

While the embodiments of the subject invention have been described and illustrated, it is obvious that various changes and modifications can be made therein without departing from the spirit of the present invention which should be limited only by the scope of the appended claims.

What is claimed is:

1. A compound of Formula 1 and a pharmaceutically acceptable salt thereof:

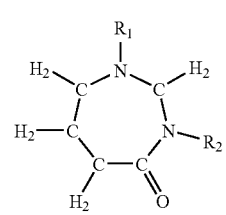

<Formula 1> wherein $R_1$ is H or $C_1$-$C_{10}$ alkyl; and $R_2$ is H or $C_1$-$C_{10}$ alkyl.

2. A pharmaceutical composition comprising the compound of claim 1 and a pharmaceutically acceptable carrier.

3. A compound of claim 1, wherein $R_1$ is H or $CH_3$; and $R_2$ is H or $CH_3$.

4. A pharmaceutical composition comprising the compound of claim 3 and a pharmaceutically acceptable carrier.

* * * * *